US011365247B2

(12) United States Patent
Ying et al.

(10) Patent No.: US 11,365,247 B2
(45) Date of Patent: Jun. 21, 2022

(54) IL-5 ANTIBODY, ANTIGEN BINDING FRAGMENT THEREOF, AND MEDICAL APPLICATION THEREFOR

(71) Applicants: Jiangsu Hengrui Medicine Co., Ltd., Jiangsu (CN); Shanghai Hengrui Pharmaceutical Co., Ltd., Shanghai (CN)

(72) Inventors: Hua Ying, Shanghai (CN); Jinping Shi, Shanghai (CN); Yifang Wang, Shanghai (CN); Qiyue Hu, Shanghai (CN); Hu Ge, Shanghai (CN); Weikang Tao, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 16/651,639

(22) PCT Filed: Sep. 28, 2018

(86) PCT No.: PCT/CN2018/108240
§ 371 (c)(1),
(2) Date: Mar. 27, 2020

(87) PCT Pub. No.: WO2019/062831
PCT Pub. Date: Apr. 4, 2019

(65) Prior Publication Data
US 2020/0262909 A1 Aug. 20, 2020

(30) Foreign Application Priority Data
Sep. 29, 2017 (CN) .......................... 201710906068.X

(51) Int. Cl.
*C07K 16/24* (2006.01)
*A61P 11/06* (2006.01)
*A61K 39/00* (2006.01)

(52) U.S. Cl.
CPC ............ *C07K 16/244* (2013.01); *A61P 11/06* (2018.01); *A61K 2039/505* (2013.01); *C07K 2317/24* (2013.01); *C07K 2317/54* (2013.01); *C07K 2317/55* (2013.01); *C07K 2317/565* (2013.01); *C07K 2317/569* (2013.01); *C07K 2317/92* (2013.01)

(58) Field of Classification Search
CPC .................................................. C07K 16/244
See application file for complete search history.

(56) References Cited

U.S. PATENT DOCUMENTS

| 5,683,892 A | 11/1997 | Ames, Jr. et al. |
| 7,982,005 B2 | 7/2011 | Ames et al. |
| 2010/0248971 A1 | 9/2010 | Inagaki et al. |

FOREIGN PATENT DOCUMENTS

| CN | 1175263 A | 3/1998 |
| CN | 100391977 C | 6/2008 |
| CN | 101883862 A | 11/2010 |
| WO | 2009068649 A2 | 6/2009 |
| WO | 2017033121 A1 | 3/2017 |

OTHER PUBLICATIONS

International Preliminary Report on Patentablity; The International Bureau of WIPO; International Application No. PCT/CN2018/108240; dated Apr. 9, 2020; 11 pages.
Safdari, Yaghoub et al.; Antibody humanization methods—a review and update; Biotechnology and Genetic Engineering Reviews; 2013; pp. 175-186; vol. 29; No. 2; Taylor & Francis.
Written Opinion of the International Searching Authority; State Intellectual Property Office of the P.R. China (ISA/CN); International Application No. PCT/CN2018/108240; dated Jan. 4, 2019; 9 pages.
International Search Report; State Intellectual Property Office of the P.R. China (ISA/CN); International Application No. PCT/CN2018/108240; dated Jan. 4, 2019; 8 pages.
Written Opinion of the International Searching Authority; State Intellectual Property Office of the P.R. China (ISA/CN); International Application No. PCT/CN2018/108240; dated Jan. 4, 2019; 4 pages.
Li-Chao Mao et al.; Research Progress of a New Agent—Mepolizumab; Wanfang Data; Practical Pharmacy and Clinical Remedies; 2016 2 pages.
Charles G. Garlisi et al.; Effects of Chronic Anti-Interleukin-5 Monoclonal Antibody Treatment in a Murine Model of Pulmonary Inflammation; American Journal of Respiratory Cell and Molecular Biology; 1999; 8 pages; vol. 20.

*Primary Examiner* — Prema M Mertz
(74) *Attorney, Agent, or Firm* — Taft Stettinius & Hollister LLP

(57) ABSTRACT

Provided are an IL-5 antibody, an antigen binding fragment thereof, and a medical application therefor. The present invention comprises a mouse-derived antibody containing an IL-5 antibody CDR region, a chimeric antibody, a humanized antibody, and a pharmaceutical composition comprising said IL-5 antibody and said antigen binding fragment thereof, as well as the use of the pharmaceutical composition as a drug.

12 Claims, 4 Drawing Sheets
Specification includes a Sequence Listing.

SEQUENCE LISTING

```
<160> NUMBER OF SEQ ID NOS: 82

<210> SEQ ID NO 1
<211> LENGTH: 140
<212> TYPE: PRT
<213> ORGANISM: Artificial sequence
<220> FEATURE:
<223> OTHER INFORMATION: Human IL-5 amino acid sequence with his tag
      (rhIL-5-his)

<400> SEQUENCE: 1

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30
```

```
Thr Leu Ala Leu Leu Ser Thr His Arg Thr Leu Leu Ile Ala Asn Glu
            35                  40                  45

Thr Leu Arg Ile Pro Val Pro Val His Lys Asn His Gln Leu Cys Thr
 50                  55                  60

Glu Glu Ile Phe Gln Gly Ile Gly Thr Leu Glu Ser Gln Thr Val Gln
 65                  70                  75                  80

Gly Gly Thr Val Glu Arg Leu Phe Lys Asn Leu Ser Leu Ile Lys Lys
                 85                  90                  95

Tyr Ile Asp Gly Gln Lys Lys Cys Gly Glu Glu Arg Arg Arg Val
            100                 105                 110

Asn Gln Phe Leu Asp Tyr Leu Gln Glu Phe Leu Gly Val Met Asn Thr
            115                 120                 125

Glu Trp Ile Ile Glu Ser His His His His His
            130                 135                 140
```

<210> SEQ ID NO 2
<211> LENGTH: 140
<212> TYPE: PRT
<213> ORGANISM: Artificial sequence
<220> FEATURE:
<223> OTHER INFORMATION: Cynomolgus monkey IL-5 amino acid sequence with his tag

<400> SEQUENCE: 2

```
Met Arg Met Leu Leu His Leu Ser Leu Leu Ala Leu Gly Ala Ala Tyr
 1               5                  10                  15

Val Tyr Ala Ile Pro Thr Glu Ile Pro Ala Ser Ala Leu Val Lys Glu
            20                  25                  30

Thr Leu Ala Leu Leu Ser Thr His Arg Thr Leu Leu Ile Ala Asn Glu
            35                  40                  45

Thr Leu Arg Ile Pro Val Pro Val His Lys Asn His Gln Leu Cys Thr
 50                  55                  60

Glu Glu Ile Phe Gln Gly Ile Gly Thr Leu Glu Ser Gln Thr Val Gln
 65                  70                  75                  80

Gly Gly Thr Val Glu Arg Leu Phe Lys Asn Leu Ser Leu Ile Lys Lys
                 85                  90                  95

Tyr Ile Gly Gly Gln Lys Lys Cys Gly Glu Glu Arg Arg Arg Val
            100                 105                 110

Asn Gln Phe Leu Asp Tyr Leu Gln Glu Phe Leu Gly Val Met Asn Thr
            115                 120                 125

Glu Trp Ile Ile Glu Ser His His His His His
            130                 135                 140
```

<210> SEQ ID NO 3
<211> LENGTH: 119
<212> TYPE: PRT
<213> ORGANISM: Artificial sequence
<220> FEATURE:
<223> OTHER INFORMATION: Mouse IL-5 amino acid sequence with his tag

<400> SEQUENCE: 3

```
Met Glu Ile Pro Met Ser Thr Val Val Lys Glu Thr Leu Thr Gln Leu
 1               5                  10                  15

Ser Ala His Arg Ala Leu Leu Thr Ser Asn Glu Thr Met Arg Leu Pro
            20                  25                  30

Val Pro Thr His Lys Asn His Gln Leu Cys Ile Gly Glu Ile Phe Gln
            35                  40                  45

Gly Leu Asp Ile Leu Lys Asn Gln Thr Val Arg Gly Gly Thr Val Glu
```

```
                50                  55                  60
Met Leu Phe Gln Asn Leu Ser Leu Ile Lys Lys Tyr Ile Asp Arg Gln
 65                  70                  75                  80

Lys Glu Lys Cys Gly Glu Arg Arg Thr Arg Gln Phe Leu Asp
                 85                  90                  95

Tyr Leu Gln Glu Phe Leu Gly Val Met Ser Thr Glu Trp Ala Met Glu
                100                 105                 110

Gly His His His His His His
                115

<210> SEQ ID NO 4
<211> LENGTH: 119
<212> TYPE: PRT
<213> ORGANISM: Artificial sequence
<220> FEATURE:
<223> OTHER INFORMATION: Rat IL-5 amino acid sequence with his tag

<400> SEQUENCE: 4

Met Glu Ile Pro Met Ser Thr Val Val Lys Glu Thr Leu Ile Gln Leu
  1               5                  10                  15

Ser Thr His Arg Ala Leu Leu Thr Ser Asn Glu Thr Met Arg Leu Pro
                 20                  25                  30

Val Pro Thr His Lys Asn His Gln Leu Cys Ile Gly Glu Ile Phe Gln
                 35                  40                  45

Gly Leu Asp Ile Leu Lys Asn Gln Thr Val Arg Gly Gly Thr Val Glu
                 50                  55                  60

Ile Leu Phe Gln Asn Leu Ser Leu Ile Lys Lys Tyr Ile Asp Gly Gln
 65                  70                  75                  80

Lys Glu Lys Cys Gly Glu Glu Arg Arg Lys Thr Arg His Phe Leu Asp
                 85                  90                  95

Tyr Leu Gln Glu Phe Leu Gly Val Met Ser Thr Glu Trp Ala Met Glu
                100                 105                 110

Val His His His His His His
                115

<210> SEQ ID NO 5
<211> LENGTH: 560
<212> TYPE: PRT
<213> ORGANISM: Artificial sequence
<220> FEATURE:
<223> OTHER INFORMATION: human IL-5 alpha fused to human Fc fragment

<400> SEQUENCE: 5

Asp Leu Leu Pro Asp Glu Lys Ile Ser Leu Leu Pro Pro Val Asn Phe
  1               5                  10                  15

Thr Ile Lys Val Thr Gly Leu Ala Gln Val Leu Leu Gln Trp Lys Pro
                 20                  25                  30

Asn Pro Asp Gln Glu Gln Arg Asn Val Asn Leu Glu Tyr Gln Val Lys
                 35                  40                  45

Ile Asn Ala Pro Lys Glu Asp Asp Tyr Glu Thr Arg Ile Thr Glu Ser
                 50                  55                  60

Lys Cys Val Thr Ile Leu His Lys Gly Phe Ser Ala Ser Val Arg Thr
 65                  70                  75                  80

Ile Leu Gln Asn Asp His Ser Leu Leu Ala Ser Ser Trp Ala Ser Ala
                 85                  90                  95

Glu Leu His Ala Pro Pro Gly Ser Pro Gly Thr Ser Ile Val Asn Leu
                100                 105                 110
```

-continued

Thr Cys Thr Thr Asn Thr Thr Glu Asp Asn Tyr Ser Arg Leu Arg Ser
        115                 120                 125

Tyr Gln Val Ser Leu His Cys Thr Trp Leu Val Gly Thr Asp Ala Pro
    130                 135                 140

Glu Asp Thr Gln Tyr Phe Leu Tyr Tyr Arg Tyr Gly Ser Trp Thr Glu
145                 150                 155                 160

Glu Cys Gln Glu Tyr Ser Lys Asp Thr Leu Gly Arg Asn Ile Ala Cys
                165                 170                 175

Trp Phe Pro Arg Thr Phe Ile Leu Ser Lys Gly Arg Asp Trp Leu Ala
            180                 185                 190

Val Leu Val Asn Gly Ser Ser Lys His Ser Ala Ile Arg Pro Phe Asp
        195                 200                 205

Gln Leu Phe Ala Leu His Ala Ile Asp Gln Ile Asn Pro Pro Leu Asn
    210                 215                 220

Val Thr Ala Glu Ile Glu Gly Thr Arg Leu Ser Ile Gln Trp Glu Lys
225                 230                 235                 240

Pro Val Ser Ala Phe Pro Ile His Cys Phe Asp Tyr Glu Val Lys Ile
                245                 250                 255

His Asn Thr Arg Asn Gly Tyr Leu Gln Ile Glu Lys Leu Met Thr Asn
            260                 265                 270

Ala Phe Ile Ser Ile Ile Asp Asp Leu Ser Lys Tyr Asp Val Gln Val
        275                 280                 285

Arg Ala Ala Val Ser Ser Met Cys Arg Glu Ala Gly Leu Trp Ser Glu
    290                 295                 300

Trp Ser Gln Pro Ile Tyr Val Gly Asn Asp Glu His Lys Pro Leu Arg
305                 310                 315                 320

Glu Trp Ile Glu Gly Arg Met Asp Glu Pro Lys Ser Cys Asp Lys Thr
                325                 330                 335

His Thr Cys Pro Pro Cys Pro Ala Pro Glu Leu Leu Gly Gly Pro Ser
            340                 345                 350

Val Phe Leu Phe Pro Pro Lys Pro Lys Asp Thr Leu Met Ile Ser Arg
        355                 360                 365

Thr Pro Glu Val Thr Cys Val Val Val Asp Val Ser His Glu Asp Pro
    370                 375                 380

Glu Val Lys Phe Asn Trp Tyr Val Asp Gly Val Glu Val His Asn Ala
385                 390                 395                 400

Lys Thr Lys Pro Arg Glu Glu Gln Tyr Asn Ser Thr Tyr Arg Val Val
                405                 410                 415

Ser Val Leu Thr Val Leu His Gln Asp Trp Leu Asn Gly Lys Glu Tyr
            420                 425                 430

Lys Cys Lys Val Ser Asn Lys Ala Leu Pro Ala Pro Ile Glu Lys Thr
        435                 440                 445

Ile Ser Lys Ala Lys Gly Gln Pro Arg Glu Pro Gln Val Tyr Thr Leu
    450                 455                 460

Pro Pro Ser Arg Asp Glu Leu Thr Lys Asn Gln Val Ser Leu Thr Cys
465                 470                 475                 480

Leu Val Lys Gly Phe Tyr Pro Ser Asp Ile Ala Val Glu Trp Glu Ser
                485                 490                 495

Asn Gly Gln Pro Glu Asn Asn Tyr Lys Thr Thr Pro Pro Val Leu Asp
            500                 505                 510

Ser Asp Gly Ser Phe Phe Leu Tyr Ser Lys Leu Thr Val Asp Lys Ser
        515                 520                 525

Arg Trp Gln Gln Gly Asn Val Phe Ser Cys Ser Val Met His Glu Ala

```
Leu His Asn His Tyr Thr Gln Lys Ser Leu Ser Leu Ser Pro Gly Lys
545                 550                 555                 560

<210> SEQ ID NO 6
<211> LENGTH: 118
<212> TYPE: PRT
<213> ORGANISM: Artificial sequence
<220> FEATURE:
<223> OTHER INFORMATION: mAb1705 murine heavy chain variable region
      sequence

<400> SEQUENCE: 6

Glu Val Gln Leu Val Glu Ser Gly Gly Gly Leu Val Gln Pro Gly Arg
1               5                   10                  15

Ser Leu Lys Leu Ser Cys Thr Ala Ser Gly Phe Thr Phe Ser His Tyr
            20                  25                  30

Tyr Met Ala Trp Val Arg Gln Ala Pro Lys Lys Gly Leu Glu Trp Val
        35                  40                  45

Thr Ser Ile Ser Tyr Glu Gly Asp Ile Thr Tyr Tyr Gly Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Ala Ser Gln Thr Leu Arg Glu Ser Phe Asp Tyr Trp Gly Gln Gly Val
            100                 105                 110

Met Val Thr Val Ser Ser
        115

<210> SEQ ID NO 7
<211> LENGTH: 107
<212> TYPE: PRT
<213> ORGANISM: Artificial sequence
<220> FEATURE:
<223> OTHER INFORMATION: mAb1705 murine light chain variable region
      sequence

<400> SEQUENCE: 7

Asp Ile Gln Met Thr Gln Ser Pro Ser Ser Met Ser Val Ser Leu Gly
1               5                   10                  15

Asp Arg Val Thr Ile Thr Cys Arg Ala Ser Gln Asp Ile Ala Asn Tyr
            20                  25                  30

Leu Ser Trp Tyr Gln Gln Lys Ile Ala Arg Ser Pro Lys Leu Val Ile
        35                  40                  45

Tyr Gly Thr Ser Asn Leu Glu Val Gly Val Pro Ser Arg Phe Ser Gly
    50                  55                  60

Ser Arg Ser Gly Ser Asp Tyr Ser Leu Thr Ile Asn Thr Leu Glu Ser
65                  70                  75                  80

Glu Asp Thr Gly Ile Tyr Phe Cys Leu Gln Asp Lys Glu Phe Pro Arg
                85                  90                  95

Thr Phe Gly Gly Gly Thr Arg Leu Glu Leu Lys
            100                 105

<210> SEQ ID NO 8
<211> LENGTH: 118
<212> TYPE: PRT
<213> ORGANISM: Artificial sequence
<220> FEATURE:
<223> OTHER INFORMATION: mAb1706 murine heavy chain variable region
``` sequence

<400> SEQUENCE: 8

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser His Tyr
            20                  25                  30

Tyr Met Ala Trp Val Arg Gln Ala Pro Lys Lys Gly Leu Glu Trp Val
        35                  40                  45

Thr Ser Ile Asn Tyr Glu Gly Asn Ser Ala Tyr Tyr Gly Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Thr Glu Thr Leu Arg Glu Ser Leu Asp Tyr Trp Gly Gln Gly Val
            100                 105                 110

Met Val Thr Val Ser Ser
        115

<210> SEQ ID NO 9
<211> LENGTH: 107
<212> TYPE: PRT
<213> ORGANISM: Artificial sequence
<220> FEATURE:
<223> OTHER INFORMATION: mAb1706 murine light chain variable region
      sequence

<400> SEQUENCE: 9

Asp Ile Gln Met Thr Gln Ser Pro Ser Ser Met Ser Val Ser Leu Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Leu Gly Lys Ser Pro Lys Leu Met Ile
        35                  40                  45

His Ser Ala Ser Asn Leu Glu Val Gly Val Pro Ser Arg Phe Ser Gly
    50                  55                  60

Ser Arg Ser Gly Ser Asp Tyr Ser Leu Thr Ile Asn Thr Leu Glu Ser
65                  70                  75                  80

Glu Asp Pro Gly Ile Tyr Phe Cys Leu Gln His Lys Gln Phe Pro Arg
                85                  90                  95

Thr Phe Gly Gly Gly Thr Lys Leu Glu Leu Lys
            100                 105

<210> SEQ ID NO 10
<211> LENGTH: 119
<212> TYPE: PRT
<213> ORGANISM: Artificial sequence
<220> FEATURE:
<223> OTHER INFORMATION: mAb1780 murine heavy chain variable region
      sequence

<400> SEQUENCE: 10

Gln Val Lys Leu Leu Gln Ser Gly Ala Ala Leu Val Lys Pro Gly Asp
1               5                   10                  15

Ser Val Lys Met Ser Cys Lys Ala Ser Asp Tyr Thr Phe Thr Glu Tyr
            20                  25                  30

Leu Ile His Trp Val Lys Gln Ser Gln Gly Arg Ser Leu Glu Trp Ile
        35                  40                  45

```
Gly Tyr Ile Asn Pro Tyr Ser Gly Gly Thr Val Tyr Asn Glu Lys Phe
        50                  55                  60

Lys Ser Lys Ala Thr Leu Thr Val Asp Lys Phe Ser Thr Ala Tyr
65                  70                  75                  80

Met Glu Phe Arg Arg Leu Thr Phe Glu Asp Ser Ala Ile Tyr Tyr Cys
                85                  90                  95

Ala Arg Asp Gly Gly Tyr Ser Asp Pro Leu Asp Tyr Trp Gly Gln Gly
                100                 105                 110

Val Met Val Thr Val Ser Ser
        115

<210> SEQ ID NO 11
<211> LENGTH: 106
<212> TYPE: PRT
<213> ORGANISM: Artificial sequence
<220> FEATURE:
<223> OTHER INFORMATION: mAb1780 murine light chain variable region
      sequence

<400> SEQUENCE: 11

Asp Thr Val Leu Thr Gln Ser Pro Ala Leu Ala Val Ser Pro Gly Glu
1               5                   10                  15

Arg Val Ser Ile Ser Cys Arg Ala Ser Glu Gly Leu Thr Ser Tyr Met
            20                  25                  30

His Trp Tyr Gln Gln Lys Pro Gly Gln Gln Pro Lys Leu Leu Ile Tyr
        35                  40                  45

Lys Ala Ser Asn Leu Ala Ser Gly Val Pro Ala Arg Phe Ser Gly Ser
    50                  55                  60

Gly Ser Gly Thr Asp Phe Thr Leu Thr Ile Asp Pro Val Glu Ala Asp
65                  70                  75                  80

Asp Ala Ala Thr Tyr Phe Cys Gln Gln Asn Trp Asn Asp Pro Trp Thr
                85                  90                  95

Phe Gly Gly Gly Thr Lys Leu Glu Leu Lys
                100                 105

<210> SEQ ID NO 12
<211> LENGTH: 116
<212> TYPE: PRT
<213> ORGANISM: Artificial sequence
<220> FEATURE:
<223> OTHER INFORMATION: mAb1773 murine heavy chain variable region
      sequence

<400> SEQUENCE: 12

Glu Val Gln Leu Gln Gln Ser Leu Ala Glu Leu Val Arg Pro Gly Ala
1               5                   10                  15

Ser Val Thr Leu Ser Cys Thr Ala Ser Gly Phe Asn Ile Lys Asn Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asp Thr Lys His Gly Pro Lys Phe
    50                  55                  60

Gln Gly Lys Ala Thr Ile Thr Ala Asp Thr Ser Ser Asn Thr Ala Tyr
65                  70                  75                  80

Leu Gln Phe Ser Ser Leu Thr Ser Glu Asp Thr Ala Ile Tyr Tyr Cys
                85                  90                  95

Phe Arg Tyr Gly Ile Tyr Pro Asp His Trp Gly Gln Gly Thr Pro Leu
                100                 105                 110
```

Thr Val Ser Ser
        115

<210> SEQ ID NO 13
<211> LENGTH: 106
<212> TYPE: PRT
<213> ORGANISM: Artificial sequence
<220> FEATURE:
<223> OTHER INFORMATION: mAb1773 murine light chain variable region
      sequence

<400> SEQUENCE: 13

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Asn Tyr Ile
            20                  25                  30

Tyr Trp Tyr Gln Gln Lys Pro Arg Ser Ser Pro Lys Pro Trp Ile Tyr
        35                  40                  45

Leu Thr Ala Thr Leu Ala Ser Gly Val Pro Ala Arg Phe Ser Gly Ser
    50                  55                  60

Gly Ser Gly Thr Ser Phe Ser Leu Thr Ile Ser Arg Met Glu Ala Glu
65                  70                  75                  80

Asp Ala Ala Thr Tyr Tyr Cys Gln Gln Trp Asn Ser Tyr Pro Tyr Thr
                85                  90                  95

Phe Gly Gly Gly Thr Lys Leu Glu Ile Glu
            100                 105

<210> SEQ ID NO 14
<211> LENGTH: 120
<212> TYPE: PRT
<213> ORGANISM: Artificial sequence
<220> FEATURE:
<223> OTHER INFORMATION: mAb1779 murine heavy chain variable region
      sequence

<400> SEQUENCE: 14

Gln Val Lys Leu Leu Gln Ser Gly Ala Ala Leu Val Lys Pro Gly Asp
1               5                   10                  15

Ser Val Lys Met Ser Cys Lys Ala Ser Gly Tyr Thr Phe Thr Asp Tyr
            20                  25                  30

Ile Ile His Trp Val Lys Gln Ser His Gly Lys Ser Leu Glu Trp Ile
        35                  40                  45

Gly Tyr Phe Asn Pro Asn Ser Gly Gly Ser Asn Tyr Asn Glu Asn Phe
    50                  55                  60

Lys Arg Lys Ala Thr Leu Thr Ala Asp Lys Ser Ser Ser Thr Ala Tyr
65                  70                  75                  80

Leu Glu Phe Ser Arg Val Thr Ser Glu Asp Ser Ala Ile Tyr Tyr Cys
                85                  90                  95

Gly Arg Arg Ile Ala Trp Asp His Trp Tyr Phe Asp Phe Trp Gly Pro
            100                 105                 110

Gly Thr Met Val Thr Val Ser Ser
        115                 120

<210> SEQ ID NO 15
<211> LENGTH: 107
<212> TYPE: PRT
<213> ORGANISM: Artificial sequence
<220> FEATURE:
<223> OTHER INFORMATION: mAb1779 murine light chain variable region
      sequence

<400> SEQUENCE: 15

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Gly Ile Ser Asn Asp
            20                  25                  30

Val Ala Trp Tyr Gln Gln Lys Ser Gly Arg Ser Pro Gln Leu Leu Val
        35                  40                  45

Tyr Ala Ala Ser Arg Leu Gln Asp Gly Val Pro Ser Arg Phe Ser Gly
    50                  55                  60

Ser Gly Ser Gly Thr Arg Tyr Phe Phe Lys Ile Ser Gly Met Gln Pro
65                  70                  75                  80

Glu Asp Glu Ala Asp Tyr Phe Cys Gln Gln Gly Tyr Lys Thr Pro Leu
                85                  90                  95

Thr Phe Gly Ser Gly Thr Lys Leu Glu Ile Lys
            100                 105

<210> SEQ ID NO 16
<211> LENGTH: 5
<212> TYPE: PRT
<213> ORGANISM: Artificial sequence
<220> FEATURE:
<223> OTHER INFORMATION: mAb1705 HCDR1

<400> SEQUENCE: 16

His Tyr Tyr Met Ala
1               5

<210> SEQ ID NO 17
<211> LENGTH: 17
<212> TYPE: PRT
<213> ORGANISM: Artificial sequence
<220> FEATURE:
<223> OTHER INFORMATION: mAb1705 HCDR2

<400> SEQUENCE: 17

Ser Ile Ser Tyr Glu Gly Asp Ile Thr Tyr Tyr Gly Asp Ser Val Lys
1               5                   10                  15

Gly

<210> SEQ ID NO 18
<211> LENGTH: 9
<212> TYPE: PRT
<213> ORGANISM: Artificial sequence
<220> FEATURE:
<223> OTHER INFORMATION: mAb1705 HCDR3

<400> SEQUENCE: 18

Gln Thr Leu Arg Glu Ser Phe Asp Tyr
1               5

<210> SEQ ID NO 19
<211> LENGTH: 11
<212> TYPE: PRT
<213> ORGANISM: Artificial sequence
<220> FEATURE:
<223> OTHER INFORMATION: mAb1705 LCDR1

<400> SEQUENCE: 19

Arg Ala Ser Gln Asp Ile Ala Asn Tyr Leu Ser
1               5                   10

```
<210> SEQ ID NO 20
<211> LENGTH: 7
<212> TYPE: PRT
<213> ORGANISM: Artificial sequence
<220> FEATURE:
<223> OTHER INFORMATION: mAb1705 LCDR2

<400> SEQUENCE: 20

Gly Thr Ser Asn Leu Glu Val
1               5

<210> SEQ ID NO 21
<211> LENGTH: 9
<212> TYPE: PRT
<213> ORGANISM: Artificial sequence
<220> FEATURE:
<223> OTHER INFORMATION: mAb1705 LCDR3

<400> SEQUENCE: 21

Leu Gln Asp Lys Glu Phe Pro Arg Thr
1               5

<210> SEQ ID NO 22
<211> LENGTH: 5
<212> TYPE: PRT
<213> ORGANISM: Artificial sequence
<220> FEATURE:
<223> OTHER INFORMATION: mAb1706 HCDR1

<400> SEQUENCE: 22

His Tyr Tyr Met Ala
1               5

<210> SEQ ID NO 23
<211> LENGTH: 17
<212> TYPE: PRT
<213> ORGANISM: Artificial sequence
<220> FEATURE:
<223> OTHER INFORMATION: mAb1706 HCDR2

<400> SEQUENCE: 23

Ser Ile Asn Tyr Glu Gly Asn Ser Ala Tyr Tyr Gly Asp Ser Val Lys
1               5                   10                  15

Gly

<210> SEQ ID NO 24
<211> LENGTH: 9
<212> TYPE: PRT
<213> ORGANISM: Artificial sequence
<220> FEATURE:
<223> OTHER INFORMATION: mAb1706 HCDR3

<400> SEQUENCE: 24

Glu Thr Leu Arg Glu Ser Leu Asp Tyr
1               5

<210> SEQ ID NO 25
<211> LENGTH: 11
<212> TYPE: PRT
<213> ORGANISM: Artificial sequence
<220> FEATURE:
<223> OTHER INFORMATION: mAb1706 LCDR1

<400> SEQUENCE: 25

Arg Ala Ser Gln Asp Ile Gly Asn Tyr Leu Ser
1               5                   10
```

```
<210> SEQ ID NO 26
<211> LENGTH: 7
<212> TYPE: PRT
<213> ORGANISM: Artificial sequence
<220> FEATURE:
<223> OTHER INFORMATION: mAb1706 LCDR2

<400> SEQUENCE: 26

Ser Ala Ser Asn Leu Glu Val
1               5

<210> SEQ ID NO 27
<211> LENGTH: 9
<212> TYPE: PRT
<213> ORGANISM: Artificial sequence
<220> FEATURE:
<223> OTHER INFORMATION: mAb1706 LCDR3

<400> SEQUENCE: 27

Leu Gln His Lys Gln Phe Pro Arg Thr
1               5

<210> SEQ ID NO 28
<211> LENGTH: 5
<212> TYPE: PRT
<213> ORGANISM: Artificial sequence
<220> FEATURE:
<223> OTHER INFORMATION: mAb1780 HCDR1

<400> SEQUENCE: 28

Glu Tyr Leu Ile His
1               5

<210> SEQ ID NO 29
<211> LENGTH: 17
<212> TYPE: PRT
<213> ORGANISM: Artificial sequence
<220> FEATURE:
<223> OTHER INFORMATION: mAb1780 HCDR2

<400> SEQUENCE: 29

Tyr Ile Asn Pro Tyr Ser Gly Gly Thr Val Tyr Asn Glu Lys Phe Lys
1               5                   10                  15

Ser

<210> SEQ ID NO 30
<211> LENGTH: 10
<212> TYPE: PRT
<213> ORGANISM: Artificial sequence
<220> FEATURE:
<223> OTHER INFORMATION: mAb1780 HCDR3

<400> SEQUENCE: 30

Asp Gly Gly Tyr Ser Asp Pro Leu Asp Tyr
1               5                   10

<210> SEQ ID NO 31
<211> LENGTH: 11
<212> TYPE: PRT
<213> ORGANISM: Artificial sequence
<220> FEATURE:
<223> OTHER INFORMATION: mAb1780 LCDR1

<400> SEQUENCE: 31

Arg Ala Ser Glu Gly Leu Thr Ser Tyr Met His
1               5                   10
```

<210> SEQ ID NO 32
<211> LENGTH: 7
<212> TYPE: PRT
<213> ORGANISM: Artificial sequence
<220> FEATURE:
<223> OTHER INFORMATION: mAb1780 LCDR2

<400> SEQUENCE: 32

Lys Ala Ser Asn Leu Ala Ser
1               5

<210> SEQ ID NO 33
<211> LENGTH: 9
<212> TYPE: PRT
<213> ORGANISM: Artificial sequence
<220> FEATURE:
<223> OTHER INFORMATION: mAb1780 LCDR3

<400> SEQUENCE: 33

Gln Gln Asn Trp Asn Asp Pro Trp Thr
1               5

<210> SEQ ID NO 34
<211> LENGTH: 5
<212> TYPE: PRT
<213> ORGANISM: Artificial sequence
<220> FEATURE:
<223> OTHER INFORMATION: mAb1773 HCDR1

<400> SEQUENCE: 34

Asn Thr Tyr Ile His
1               5

<210> SEQ ID NO 35
<211> LENGTH: 17
<212> TYPE: PRT
<213> ORGANISM: Artificial sequence
<220> FEATURE:
<223> OTHER INFORMATION: mAb1773 HCDR2

<400> SEQUENCE: 35

Arg Ile Asp Pro Ala Asn Gly Asp Thr Lys His Gly Pro Lys Phe Gln
1               5                   10                  15

Gly

<210> SEQ ID NO 36
<211> LENGTH: 7
<212> TYPE: PRT
<213> ORGANISM: Artificial sequence
<220> FEATURE:
<223> OTHER INFORMATION: mAb1773 HCDR3

<400> SEQUENCE: 36

Tyr Gly Ile Tyr Pro Asp His
1               5

<210> SEQ ID NO 37
<211> LENGTH: 10
<212> TYPE: PRT
<213> ORGANISM: Artificial sequence
<220> FEATURE:
<223> OTHER INFORMATION: mAb1773 LCDR1

<400> SEQUENCE: 37

Ser Ala Ser Ser Ser Val Asn Tyr Ile Tyr

```
1               5                   10
```

<210> SEQ ID NO 38
<211> LENGTH: 7
<212> TYPE: PRT
<213> ORGANISM: Artificial sequence
<220> FEATURE:
<223> OTHER INFORMATION: mAb1773 LCDR2

<400> SEQUENCE: 38

```
Leu Thr Ala Thr Leu Ala Ser
1               5
```

<210> SEQ ID NO 39
<211> LENGTH: 9
<212> TYPE: PRT
<213> ORGANISM: Artificial sequence
<220> FEATURE:
<223> OTHER INFORMATION: mAb1773 LCDR3

<400> SEQUENCE: 39

```
Gln Gln Trp Asn Ser Tyr Pro Tyr Thr
1               5
```

<210> SEQ ID NO 40
<211> LENGTH: 5
<212> TYPE: PRT
<213> ORGANISM: Artificial sequence
<220> FEATURE:
<223> OTHER INFORMATION: mAb1779 HCDR1

<400> SEQUENCE: 40

```
Asp Tyr Ile Ile His
1               5
```

<210> SEQ ID NO 41
<211> LENGTH: 17
<212> TYPE: PRT
<213> ORGANISM: Artificial sequence
<220> FEATURE:
<223> OTHER INFORMATION: mAb1779 HCDR2

<400> SEQUENCE: 41

```
Tyr Phe Asn Pro Asn Ser Gly Gly Ser Asn Tyr Asn Glu Asn Phe Lys
1               5                   10                  15
Arg
```

<210> SEQ ID NO 42
<211> LENGTH: 11
<212> TYPE: PRT
<213> ORGANISM: Artificial sequence
<220> FEATURE:
<223> OTHER INFORMATION: mAb1779 HCDR3

<400> SEQUENCE: 42

```
Arg Ile Ala Trp Asp His Trp Tyr Phe Asp Phe
1               5                   10
```

<210> SEQ ID NO 43
<211> LENGTH: 11
<212> TYPE: PRT
<213> ORGANISM: Artificial sequence
<220> FEATURE:
<223> OTHER INFORMATION: mAb1779 LCDR1

<400> SEQUENCE: 43

Leu Ala Ser Glu Gly Ile Ser Asn Asp Val Ala
1               5                   10

<210> SEQ ID NO 44
<211> LENGTH: 7
<212> TYPE: PRT
<213> ORGANISM: Artificial sequence
<220> FEATURE:
<223> OTHER INFORMATION: mAb1779 LCDR2

<400> SEQUENCE: 44

Ala Ala Ser Arg Leu Gln Asp
1               5

<210> SEQ ID NO 45
<211> LENGTH: 9
<212> TYPE: PRT
<213> ORGANISM: Artificial sequence
<220> FEATURE:
<223> OTHER INFORMATION: mAb1779 LCDR3

<400> SEQUENCE: 45

Gln Gln Gly Tyr Lys Thr Pro Leu Thr
1               5

<210> SEQ ID NO 46
<211> LENGTH: 107
<212> TYPE: PRT
<213> ORGANISM: Artificial sequence
<220> FEATURE:
<223> OTHER INFORMATION: h1705_VL.1

<400> SEQUENCE: 46

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ala Asn Tyr
            20                  25                  30

Leu Ser Trp Tyr Gln Gln Lys Pro Gly Lys Ala Pro Lys Leu Leu Ile
        35                  40                  45

Tyr Gly Thr Ser Asn Leu Glu Val Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Lys Glu Phe Pro Arg
                85                  90                  95

Thr Phe Gly Gly Gly Thr Lys Val Glu Ile Lys
            100                 105

<210> SEQ ID NO 47
<211> LENGTH: 107
<212> TYPE: PRT
<213> ORGANISM: Artificial sequence
<220> FEATURE:
<223> OTHER INFORMATION: h1705_VL.1A

<400> SEQUENCE: 47

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ala Asn Tyr
            20                  25                  30

Leu Ser Trp Tyr Gln Gln Lys Pro Gly Lys Ser Pro Lys Leu Leu Ile
        35                  40                  45

```
Tyr Gly Thr Ser Asn Leu Glu Val Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Lys Glu Phe Pro Arg
                85                  90                  95

Thr Phe Gly Gly Gly Thr Lys Val Glu Ile Lys
                100                 105
```

```
<210> SEQ ID NO 48
<211> LENGTH: 107
<212> TYPE: PRT
<213> ORGANISM: Artificial sequence
<220> FEATURE:
<223> OTHER INFORMATION: h1705_VL.1B

<400> SEQUENCE: 48

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ala Asn Tyr
            20                  25                  30

Leu Ser Trp Tyr Gln Gln Lys Pro Gly Lys Ser Pro Lys Leu Val Ile
        35                  40                  45

Tyr Gly Thr Ser Asn Leu Glu Val Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Phe Cys Leu Gln Asp Lys Glu Phe Pro Arg
                85                  90                  95

Thr Phe Gly Gly Gly Thr Lys Val Glu Ile Lys
                100                 105
```

```
<210> SEQ ID NO 49
<211> LENGTH: 118
<212> TYPE: PRT
<213> ORGANISM: Artificial sequence
<220> FEATURE:
<223> OTHER INFORMATION: h1705_VH.1

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45

Ser Ser Ile Ser Tyr Glu Gly Asp Ile Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Thr Leu Arg Glu Ser Phe Asp Tyr Trp Gly Gln Gly Thr
                100                 105                 110

Leu Val Thr Val Ser Ser
        115
```

```
<210> SEQ ID NO 50
```

```
<211> LENGTH: 118
<212> TYPE: PRT
<213> ORGANISM: Artificial sequence
<220> FEATURE:
<223> OTHER INFORMATION: h1705_VH.1A

<400> SEQUENCE: 50
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45

Ser Ser Ile Ser Tyr Glu Gly Asp Ile Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gln Thr Leu Arg Glu Ser Phe Asp Tyr Trp Gly Gln Gly Thr
            100                 105                 110

Leu Val Thr Val Ser Ser
        115

```
<210> SEQ ID NO 51
<211> LENGTH: 118
<212> TYPE: PRT
<213> ORGANISM: Artificial sequence
<220> FEATURE:
<223> OTHER INFORMATION: h1705_VH.1B

<400> SEQUENCE: 51
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45

Thr Ser Ile Ser Tyr Glu Gly Asp Ile Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Ser Gln Thr Leu Arg Glu Ser Phe Asp Tyr Trp Gly Gln Gly Thr
            100                 105                 110

Leu Val Thr Val Ser Ser
        115

```
<210> SEQ ID NO 52
<211> LENGTH: 330
<212> TYPE: PRT
<213> ORGANISM: Artificial sequence
<220> FEATURE:
<223> OTHER INFORMATION: Heavy chain IgG1 constant region

<400> SEQUENCE: 52
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 53
<211> LENGTH: 107
<212> TYPE: PRT
<213> ORGANISM: Artificial sequence
<220> FEATURE:
<223> OTHER INFORMATION: Light chain kappa constant region

<400> SEQUENCE: 53

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

-continued

Ser Gly Asn Ser Gln Glu Ser Val Thr Glu Gln Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 54
<211> LENGTH: 107
<212> TYPE: PRT
<213> ORGANISM: Artificial sequence
<220> FEATURE:
<223> OTHER INFORMATION: h1706_VL.1

<400> SEQUENCE: 54

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Asp Ile Gly Asn Tyr
                 20                  25                  30

Leu Ser Trp Tyr Gln Gln Lys Pro Gly Lys Ala Pro Lys Leu Leu Ile
             35                  40                  45

Tyr Ser Ala Ser Asn Leu Glu Val Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Lys Gln Phe Pro Arg
                 85                  90                  95

Thr Phe Gly Gly Gly Thr Lys Val Glu Ile Lys
            100                 105

<210> SEQ ID NO 55
<211> LENGTH: 107
<212> TYPE: PRT
<213> ORGANISM: Artificial sequence
<220> FEATURE:
<223> OTHER INFORMATION: h1706_VL.1A

<400> SEQUENCE: 55

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Asp Ile Gly Asn Tyr
                 20                  25                  30

Leu Ser Trp Tyr Gln Gln Lys Pro Gly Lys Ser Pro Lys Leu Leu Ile
             35                  40                  45

Tyr Ser Ala Ser Asn Leu Glu Val Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Lys Gln Phe Pro Arg
                 85                  90                  95

Thr Phe Gly Gly Gly Thr Lys Val Glu Ile Lys
            100                 105

<210> SEQ ID NO 56
<211> LENGTH: 107
<212> TYPE: PRT
<213> ORGANISM: Artificial sequence

```
<220> FEATURE:
<223> OTHER INFORMATION: h1706_VL.1B

<400> SEQUENCE: 56

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ser Pro Lys Leu Met Ile
        35                  40                  45

Tyr Ser Ala Ser Asn Leu Glu Val Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Lys Gln Phe Pro Arg
                85                  90                  95

Thr Phe Gly Gly Gly Thr Lys Val Glu Ile Lys
            100                 105

<210> SEQ ID NO 57
<211> LENGTH: 118
<212> TYPE: PRT
<213> ORGANISM: Artificial sequence
<220> FEATURE:
<223> OTHER INFORMATION: h1706_VH.1

<400> SEQUENCE: 57

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45

Ser Ser Ile Asn Tyr Glu Gly Asn Ser Ala Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Thr Leu Arg Glu Ser Leu Asp Tyr Trp Gly Gln Gly Thr
            100                 105                 110

Met Val Thr Val Ser Ser
        115

<210> SEQ ID NO 58
<211> LENGTH: 118
<212> TYPE: PRT
<213> ORGANISM: Artificial sequence
<220> FEATURE:
<223> OTHER INFORMATION: h1706_VH.1A

<400> SEQUENCE: 58

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45
```

```
Ser Ser Ile Asn Tyr Glu Gly Asn Ser Ala Tyr Tyr Gly Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Glu Thr Leu Arg Glu Ser Leu Asp Tyr Trp Gly Gln Gly Thr
            100                 105                 110

Met Val Thr Val Ser Ser
            115

<210> SEQ ID NO 59
<211> LENGTH: 118
<212> TYPE: PRT
<213> ORGANISM: Artificial sequence
<220> FEATURE:
<223> OTHER INFORMATION: h1706_VH.1B

<400> SEQUENCE: 59

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser His Tyr
                 20                  25                  30

Tyr Met Ala Trp Val Arg Gln Ala Pro Gly Lys Gly Leu Glu Trp Val
             35                  40                  45

Thr Ser Ile Asn Tyr Glu Gly Asn Ser Ala Tyr Tyr Gly Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Thr Glu Thr Leu Arg Glu Ser Leu Asp Tyr Trp Gly Gln Gly Thr
            100                 105                 110

Met Val Thr Val Ser Ser
            115

<210> SEQ ID NO 60
<211> LENGTH: 107
<212> TYPE: PRT
<213> ORGANISM: Artificial sequence
<220> FEATURE:
<223> OTHER INFORMATION: h1780_VL.1

<400> SEQUENCE: 60

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Glu Gly Leu Thr Ser Tyr
                 20                  25                  30

Met His Trp Tyr Gln Gln Lys Pro Gly Gln Ala Pro Arg Leu Leu Ile
             35                  40                  45

Tyr Lys Ala Ser Asn Leu Ala Ser Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Asn Trp Asn Asp Pro Trp
                 85                  90                  95

Thr Phe Gly Gly Gly Thr Lys Val Glu Ile Lys
            100                 105
```

<210> SEQ ID NO 61
<211> LENGTH: 107
<212> TYPE: PRT
<213> ORGANISM: Artificial sequence
<220> FEATURE:
<223> OTHER INFORMATION: h1780_VL.1A

<400> SEQUENCE: 61

Asp Thr Val Leu Thr Gln Ser Pro Ala Thr Leu Ser Leu Ser Pro Gly
1               5                   10                  15

Glu Arg Ala Thr Leu Ser Cys Arg Ala Ser Glu Gly Leu Thr Ser Tyr
            20                  25                  30

Met His Trp Tyr Gln Gln Lys Pro Gly Gln Ala Pro Arg Leu Leu Ile
        35                  40                  45

Tyr Lys Ala Ser Asn Leu Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asn Trp Asn Asp Pro Trp
                85                  90                  95

Thr Phe Gly Gly Gly Thr Lys Val Glu Ile Lys
            100                 105

<210> SEQ ID NO 62
<211> LENGTH: 107
<212> TYPE: PRT
<213> ORGANISM: Artificial sequence
<220> FEATURE:
<223> OTHER INFORMATION: h1780_VL.1B

<400> SEQUENCE: 62

Asp Thr Val Leu Thr Gln Ser Pro Ala Thr Leu Ser Leu Ser Pro Gly
1               5                   10                  15

Glu Arg Ala Thr Leu Ser Cys Arg Ala Ser Glu Gly Leu Thr Ser Tyr
            20                  25                  30

Met His Trp Tyr Gln Gln Lys Pro Gly Gln Ala Pro Arg Leu Leu Ile
        35                  40                  45

Tyr Lys Ala Ser Asn Leu Ala Ser Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Phe Cys Gln Gln Asn Trp Asn Asp Pro Trp
                85                  90                  95

Thr Phe Gly Gly Gly Thr Lys Val Glu Ile Lys
            100                 105

<210> SEQ ID NO 63
<211> LENGTH: 119
<212> TYPE: PRT
<213> ORGANISM: Artificial sequence
<220> FEATURE:
<223> OTHER INFORMATION: h1780_VH.1

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

```
Leu Ile His Trp Val Arg Gln Ala Pro Gly Gln Gly Leu Glu Trp Met
            35                  40                  45

Gly Tyr Ile Asn Pro Tyr Ser Gly Gly Thr Val Tyr Asn Glu Lys Phe
 50                  55                  60

Lys Ser Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Gly Gly Tyr Ser Asp Pro Leu Asp Tyr Trp Gly Gln Gly
                100                 105                 110

Thr Met Val Thr Val Ser Ser
            115
```

<210> SEQ ID NO 64
<211> LENGTH: 119
<212> TYPE: PRT
<213> ORGANISM: Artificial sequence
<220> FEATURE:
<223> OTHER INFORMATION: h1780_VH.1A

<400> SEQUENCE: 64

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu Tyr
                 20                  25                  30

Leu Ile His Trp Val Arg Gln Ala Pro Gly Gln Gly Leu Glu Trp Met
            35                  40                  45

Gly Tyr Ile Asn Pro Tyr Ser Gly Gly Thr Val Tyr Asn Glu Lys Phe
 50                  55                  60

Lys Ser Arg Val Thr Leu Thr Val Asp Lys Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Gly Gly Tyr Ser Asp Pro Leu Asp Tyr Trp Gly Gln Gly
                100                 105                 110

Thr Met Val Thr Val Ser Ser
            115
```

<210> SEQ ID NO 65
<211> LENGTH: 119
<212> TYPE: PRT
<213> ORGANISM: Artificial sequence
<220> FEATURE:
<223> OTHER INFORMATION: h1780_VH.1B

<400> SEQUENCE: 65

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu Tyr
                 20                  25                  30

Leu Ile His Trp Val Arg Gln Ala Pro Gly Gln Gly Leu Glu Trp Ile
            35                  40                  45

Gly Tyr Ile Asn Pro Tyr Ser Gly Gly Thr Val Tyr Asn Glu Lys Phe
 50                  55                  60

Lys Ser Arg Ala Thr Leu Thr Val Asp Lys Ser Ile Ser Thr Ala Tyr
 65                  70                  75                  80

Met Glu Phe Ser Arg Leu Arg Ser Asp Asp Thr Ala Val Tyr Tyr Cys
                 85                  90                  95
```

Ala Arg Asp Gly Gly Tyr Ser Asp Pro Leu Asp Tyr Trp Gln Gly
            100                 105                 110

Thr Met Val Thr Val Ser Ser
        115

<210> SEQ ID NO 66
<211> LENGTH: 119
<212> TYPE: PRT
<213> ORGANISM: Artificial sequence
<220> FEATURE:
<223> OTHER INFORMATION: h1780_VH.1C

<400> SEQUENCE: 66

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Leu Ile His Trp Val Lys Gln Ala Pro Gly Gln Gly Leu Glu Trp Ile
        35                  40                  45

Gly Tyr Ile Asn Pro Tyr Ser Gly Gly Thr Val Tyr Asn Glu Lys Phe
    50                  55                  60

Lys Ser Lys Ala Thr Leu Thr Val Asp Lys Ser Ile Ser Thr Ala Tyr
65                  70                  75                  80

Met Glu Phe Ser Arg Leu Arg Ser Asp Asp Thr Ala Val Tyr Tyr Cys
                85                  90                  95

Ala Arg Asp Gly Gly Tyr Ser Asp Pro Leu Asp Tyr Trp Gln Gly
            100                 105                 110

Thr Met Val Thr Val Ser Ser
        115

<210> SEQ ID NO 67
<211> LENGTH: 106
<212> TYPE: PRT
<213> ORGANISM: Artificial sequence
<220> FEATURE:
<223> OTHER INFORMATION: h1773_VL.1

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Asn Tyr Ile
            20                  25                  30

Tyr Trp Tyr Gln Gln Lys Pro Gly Lys Ala Pro Lys Leu Leu Ile Tyr
        35                  40                  45

Leu Thr Ala Thr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asn Ser Tyr Pro Tyr Thr
                85                  90                  95

Phe Gly Gly Gly Thr Lys Val Glu Ile Lys
            100                 105

<210> SEQ ID NO 68
<211> LENGTH: 106
<212> TYPE: PRT
<213> ORGANISM: Artificial sequence
<220> FEATURE:
<223> OTHER INFORMATION: h1773_VL.1A

```
<400> SEQUENCE: 68

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Asn Tyr Ile
            20                  25                  30

Tyr Trp Tyr Gln Gln Lys Pro Gly Lys Ser Pro Lys Pro Trp Ile Tyr
            35                  40                  45

Leu Thr Ala Thr Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asn Ser Tyr Pro Tyr Thr
                85                  90                  95

Phe Gly Gly Gly Thr Lys Val Glu Ile Lys
            100                 105

<210> SEQ ID NO 69
<211> LENGTH: 116
<212> TYPE: PRT
<213> ORGANISM: Artificial sequence
<220> FEATURE:
<223> OTHER INFORMATION: h1773_VH.1

<400> SEQUENCE: 69

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Thr
            20                  25                  30

Tyr Ile His Trp Val Arg Gln Ala Ser Gly Lys Gly Leu Glu Trp Val
            35                  40                  45

Gly Arg Ile Asp Pro Ala Val Gly Asp Thr Lys His Gly Pro Lys Phe
        50                  55                  60

Gln Gly Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Thr Arg Tyr Gly Ile Tyr Pro Asp His Trp Gly Gln Gly Thr Leu Val
            100                 105                 110

Thr Val Ser Ser
        115

<210> SEQ ID NO 70
<211> LENGTH: 116
<212> TYPE: PRT
<213> ORGANISM: Artificial sequence
<220> FEATURE:
<223> OTHER INFORMATION: h1773_VH.1A

<400> SEQUENCE: 70

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Ile Ser Asn Thr
            20                  25                  30

Tyr Ile His Trp Val Arg Gln Ala Ser Gly Lys Gly Leu Glu Trp Val
            35                  40                  45

Gly Arg Ile Asp Pro Ala Val Gly Asp Thr Lys His Gly Pro Lys Phe
        50                  55                  60
```

Gln Gly Arg Phe Thr Ile Ser Ala Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Phe Arg Tyr Gly Ile Tyr Pro Asp His Trp Gly Gln Gly Thr Leu Val
            100                 105                 110

Thr Val Ser Ser
        115

<210> SEQ ID NO 71
<211> LENGTH: 116
<212> TYPE: PRT
<213> ORGANISM: Artificial sequence
<220> FEATURE:
<223> OTHER INFORMATION: h1773_VH.1B

<400> SEQUENCE: 71

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Ile Ser Asn Thr
            20                  25                  30

Tyr Ile His Trp Val Lys Gln Ala Ser Gly Lys Gly Leu Glu Trp Ile
        35                  40                  45

Gly Arg Ile Asp Pro Ala Val Gly Asp Thr Lys His Gly Pro Lys Phe
    50                  55                  60

Gln Gly Arg Phe Thr Ile Ser Ala Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Phe Arg Tyr Gly Ile Tyr Pro Asp His Trp Gly Gln Gly Thr Leu Val
            100                 105                 110

Thr Val Ser Ser
        115

<210> SEQ ID NO 72
<211> LENGTH: 107
<212> TYPE: PRT
<213> ORGANISM: Artificial sequence
<220> FEATURE:
<223> OTHER INFORMATION: h1779_VL.1

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Asn Asp
            20                  25                  30

Val Ala Trp Tyr Gln Gln Lys Pro Gly Lys Ala Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Tyr Lys Thr Pro Leu
                85                  90                  95

Thr Phe Gly Gln Gly Thr Lys Leu Glu Ile Lys
            100                 105

<210> SEQ ID NO 73
<211> LENGTH: 107
<212> TYPE: PRT
<213> ORGANISM: Artificial sequence
<220> FEATURE:
<223> OTHER INFORMATION: h1779_VL.1A

<400> SEQUENCE: 73

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Asn Asp
            20                  25                  30

Val Ala Trp Tyr Gln Gln Lys Pro Gly Lys Ser Pro Lys Leu Leu Ile
        35                  40                  45

Tyr Ala Ala Ser Arg Leu Gln Asp Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Tyr Lys Thr Pro Leu
                85                  90                  95

Thr Phe Gly Gln Gly Thr Lys Leu Glu Ile Lys
            100                 105
```

<210> SEQ ID NO 74
<211> LENGTH: 107
<212> TYPE: PRT
<213> ORGANISM: Artificial sequence
<220> FEATURE:
<223> OTHER INFORMATION: h1779_VL.1B

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Asn Asp
            20                  25                  30

Val Ala Trp Tyr Gln Gln Lys Pro Gly Lys Ser Pro Lys Leu Leu Val
        35                  40                  45

Tyr Ala Ala Ser Arg Leu Gln Asp Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Tyr Lys Thr Pro Leu
                85                  90                  95

Thr Phe Gly Gln Gly Thr Lys Leu Glu Ile Lys
            100                 105
```

<210> SEQ ID NO 75
<211> LENGTH: 120
<212> TYPE: PRT
<213> ORGANISM: Artificial sequence
<220> FEATURE:
<223> OTHER INFORMATION: h1779_VH.1

<400> SEQUENCE: 75

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Ile His Trp Val Arg Gln Ala Pro Gly Gln Gly Leu Glu Trp Met
        35                  40                  45
```

Gly Tyr Phe Asn Pro Asn Ser Gly Ser Asn Tyr Asn Glu Asn Phe
            50                  55                  60

Lys Arg Arg Val Thr Met Thr Arg Asp Thr Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Arg Ile Ala Trp Asp His Trp Tyr Phe Asp Phe Trp Gly Gln
                100                 105                 110

Gly Thr Met Val Thr Val Ser Ser
            115                 120

<210> SEQ ID NO 76
<211> LENGTH: 120
<212> TYPE: PRT
<213> ORGANISM: Artificial sequence
<220> FEATURE:
<223> OTHER INFORMATION: h1779_VH.1A

<400> SEQUENCE: 76

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                 20                  25                  30

Ile Ile His Trp Val Arg Gln Ala Pro Gly Gln Gly Leu Glu Trp Met
             35                  40                  45

Gly Tyr Phe Asn Pro Asn Ser Gly Ser Asn Tyr Asn Glu Asn Phe
            50                  55                  60

Lys Arg Arg Val Thr Met Thr Ala Asp Lys Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Arg Ile Ala Trp Asp His Trp Tyr Phe Asp Phe Trp Gly Gln
                100                 105                 110

Gly Thr Met Val Thr Val Ser Ser
            115                 120

<210> SEQ ID NO 77
<211> LENGTH: 120
<212> TYPE: PRT
<213> ORGANISM: Artificial sequence
<220> FEATURE:
<223> OTHER INFORMATION: h1779_VH.1B

<400> SEQUENCE: 77

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                 20                  25                  30

Ile Ile His Trp Val Arg Gln Ala Pro Gly Gln Gly Leu Glu Trp Ile
             35                  40                  45

Gly Tyr Phe Asn Pro Asn Ser Gly Ser Asn Tyr Asn Glu Asn Phe
            50                  55                  60

Lys Arg Arg Ala Thr Met Thr Ala Asp Lys Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Arg Ile Ala Trp Asp His Trp Tyr Phe Asp Phe Trp Gly Gln

```
<210> SEQ ID NO 78
<211> LENGTH: 120
<212> TYPE: PRT
<213> ORGANISM: Artificial sequence
<220> FEATURE:
<223> OTHER INFORMATION: h1779_VH.1C

<400> SEQUENCE: 78

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Ile His Trp Val Arg Gln Ala Pro Gly Gln Gly Leu Glu Trp Ile
        35                  40                  45

Gly Tyr Phe Asn Pro Asn Ser Gly Gly Ser Asn Tyr Asn Glu Asn Phe
    50                  55                  60

Lys Arg Arg Ala Thr Met Thr Ala Asp Lys Ser Ile Ser Thr Ala Tyr
65                  70                  75                  80

Leu Glu Phe Ser Arg Leu Arg Ser Glu Asp Thr Ala Val Tyr Tyr Cys
                85                  90                  95

Ala Arg Arg Ile Ala Trp Asp His Trp Tyr Phe Asp Phe Trp Gly Gln
            100                 105                 110

Gly Thr Met Val Thr Val Ser Ser
        115                 120

<210> SEQ ID NO 79
<211> LENGTH: 120
<212> TYPE: PRT
<213> ORGANISM: Artificial sequence
<220> FEATURE:
<223> OTHER INFORMATION: h1779_VH.1D

<400> SEQUENCE: 79

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Ile His Trp Val Lys Gln Ala Pro Gly Gln Gly Leu Glu Trp Ile
        35                  40                  45

Gly Tyr Phe Asn Pro Asn Ser Gly Gly Ser Asn Tyr Asn Glu Asn Phe
    50                  55                  60

Lys Arg Lys Ala Thr Met Thr Ala Asp Lys Ser Ile Ser Thr Ala Tyr
65                  70                  75                  80

Leu Glu Phe Ser Arg Leu Arg Ser Glu Asp Thr Ala Val Tyr Tyr Cys
                85                  90                  95

Ala Arg Arg Ile Ala Trp Asp His Trp Tyr Phe Asp Phe Trp Gly Gln
            100                 105                 110

Gly Thr Met Val Thr Val Ser Ser
        115                 120

<210> SEQ ID NO 80
<211> LENGTH: 443
<212> TYPE: PRT
<213> ORGANISM: Artificial sequence
<220> FEATURE:
```

<223> OTHER INFORMATION: Heavy chain sequence of Hu39D10

<400> SEQUENCE: 80

```
Glu Val Gln Leu Val Glu Ser Gly Gly Gly Leu Val Gln Pro Gly Gly
 1               5                  10                  15

Ser Leu Arg Leu Ser Cys Ala Val Ser Gly Leu Ser Thr Ser Asn
             20                  25                  30

Ser Val Asn Trp Ile Arg Gln Ala Pro Gly Lys Gly Leu Glu Trp Val
         35                  40                  45

Gly Leu Ile Trp Ser Asn Gly Asp Thr Asp Tyr Asn Ser Ala Ile Lys
     50                  55                  60

Ser Arg Phe Thr Ile Ser Arg Asp Thr Ser Lys Ser Thr Val Tyr Leu
 65                  70                  75                  80

Gln Met Asn Ser Leu Arg Ala Glu Asp Thr Ala Val Tyr Tyr Cys Ala
                 85                  90                  95

Arg Glu Tyr Tyr Gly Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400
```

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
        420                 425                 430

Thr Gln Lys Ser Leu Ser Leu Ser Leu Gly Lys
        435                 440

<210> SEQ ID NO 81
<211> LENGTH: 214
<212> TYPE: PRT
<213> ORGANISM: Artificial sequence
<220> FEATURE:
<223> OTHER INFORMATION: Light chain sequence of Hu39D10

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Asn Ser Leu Gln Thr Gly Val Pro Ser Arg Phe Ser Gly
    50                  55                  60

Ser Gly Ser Ala Thr Asp Tyr Thr Leu Thr Ile Ser Ser Leu Gln Pro
65                  70                  75                  80

Glu Asp Phe Ala Thr Tyr Tyr Cys Gln Gln Ser Tyr Lys Phe Pro Asn
                85                  90                  95

Thr Phe Gly Gln Gly Thr Lys Val Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 82
<211> LENGTH: 17
<212> TYPE: PRT
<213> ORGANISM: Artificial sequence
<220> FEATURE:
<223> OTHER INFORMATION: h1773 antibody body heavy chain HCDR2 variant

<400> SEQUENCE: 82

Arg Ile Asp Pro Ala Val Gly Asp Thr Lys His Gly Pro Lys Phe Gln
1               5                   10                  15

Gly

IL-5 ANTIBODY, ANTIGEN BINDING FRAGMENT THEREOF, AND MEDICAL APPLICATION THEREFOR

CROSS-REFERENCE TO RELATED APPLICATIONS

This application is a U.S. National Phase of International PCT Application No. PCT/CN2018/108240 filed Sep. 28, 2018, which claims the benefit of Chinese Patent Application Serial No. 201710906068.X filed Sep. 29, 2017, the contents of each application are incorporated herein by reference in their entirety.

FIELD OF THE INVENTION

The present disclosure relates to IL-5 antibodies and antigen-binding fragments thereof. Further, the present disclosure also relates to chimeric antibodies, humanized antibodies comprising the CDR regions of the IL-5 antibodies, and the present disclosure also relates to a pharmaceutical composition comprising the IL-5 antibody and antigen-binding fragment thereof, and its use as a diagnostic and therapeutic agent for IL-5-related diseases.

BACKGROUND OF THE INVENTION

Interleukin-5 (IL-5) is one of the important members of the interleukin family, also known as T cell replacing factor (TRF), B cell growth factor-II (BCGF-II), IgA-enhancing factor (IgA-EF), or eosinophil differentiation factor (EDF). It is a homodimeric glycoprotein secreted mainly by helper T cell 2 (Th2). Human IL-5 consists of 134 amino acid residues, including a signal peptide consisting of 22 amino acids and two glycosylation sites. Human IL-5 has 70% identity with murine IL-5 on amino acid level. An active IL-5 is in the form of oligodimer, with two peptide chains linked to each other via disulfide bond(s) and in an antiparallel configuration, while the monomers of IL-5 are not biologically active (Adv Immunol. 1994; 57:145-90).

Eosinophil (EOS) is associated with a variety of inflammatory diseases in lung, including allergic diseases associated with anaphylactic reaction. Among these diseases, asthma is a chronic respiratory inflammatory disease, affecting approximately 300 million patients worldwide, with a morbidity of 10%. Its pathogenesis is associated with a variety of cytokines, and IL-5 and its receptor IL-5R play an important role in the pathogenesis of asthma. There is a large amount of inflammatory cells infiltrating in the bronchopulmonary tissue of patients with asthma, among which eosinophils are most significantly increased. Many studies have shown that eosinophil is one of the major cells leading to airway inflammation in asthma (Curr Opin Pulm Med. 2005 January; 11(1): 1-6). IL-5 plays an extremely important role in the differentiation, maturation, adhesion, infiltration and apoptosis of EOS. A large number of animal studies and clinical studies have shown that IL-5 can activate EOS progenitor cells in the bone marrow and initiate the aggregation of EOS in peripheral blood and airway, leading to chronic inflammation and hyperresponsiveness of the airway (J Immunol. 2014 Oct. 15; 193(8):4043-52). In addition, IL-5 can prolong the survival duration of EOS, enhance its degranulation response to specific stimulating factors (such as IgA or IgG), and mediate the chemotactic activity of eosinophils (J Asthma Allergy. 2015 Nov. 3; 8: 125-34). Increased expression of IL-5 was detected in both asthma patients and human bronchial antigen-induced models (Greenfeder et al, Respiratory Research, 2: 71-79, 2001). The recombinant human IL-5 protein taken by asthma patients will result in the increased number of eosinophils, the bronchial hyperresponsiveness, and release of toxic particles by eosinophils, indicating that IL-5 is a key factor in the pathogenesis of asthma.

Currently, the most effective method for the treatment of asthma is to inhibit the expression of some key mediators (including IL-5) in asthma via nasal or oral administration of sterols to alleviate inflammation in lung. However, long-term use of sterols has many side effects. It is therefore necessary to find new pharmaceutical targets 50 for the treatment of asthma. Studies have shown that by inhibiting the binding of IL-5 to its receptor, IL-5 antibodies can significantly reduce the accumulation of eosinophils in lung, reduce the level of eosinophils in blood, tissue and sputum, decrease the eosinophil-mediated inflammatory response, improve lung function, and exhibit good efficacy for the treatment of severe eosinophil asthma and recurrent asthma (Drugs, 2017 May; 77(7): 777-784). Currently, only IL-5 antibodies mepolizumab from GSK and reslizumab from Teva Pharma are commercially available. Other antibodies against the IL-5 target are in preclinical research phase. The related patents are for example, WO2017033121, WO2016040007, WO2015095539, WO2012083370, WO2012158954, WO2006046689, WO9621000, WO9535375, etc., However, there is still a need for the improvement in IL-5-induced elimination of eosinophils and the improvement of lung function. Therefore, it is necessary to continue to develop antibodies with high selectivity, high affinity and good efficacy to provide more and preferred anti-IL-5 treatment regimens for asthma.

SUMMARY OF THE INVENTION

The present disclosure provides monoclonal antibodies or antigen-binding fragments (also referred to as IL-5 binding molecules) that specifically bind to the amino acid sequence of IL-5 or three-dimensional structure.

In one aspect, the disclosure provides a monoclonal antibody or antigen-binding fragment thereof binding to human IL-5, wherein the monoclonal antibody comprises a heavy chain variable region and a light chain variable region, wherein, (i) the heavy chain variable region comprises HCDR1. HCDR2 and HCDR3 region as set forth in amino acid sequences of SEQ ID NOs: 16-18, or HCDR variants having 3, 2, or 1 amino acid difference(s) from HCDR1. HCDR2 and HCDR3 region as set forth in SEQ ID NOs: 16-18, respectively; and the light chain variable region comprises LCDR1, LCDR2 and LCDR3 region as set forth in amino acid sequences of SEQ ID NOs: 19-21, or LCDR variants having 3, 2, or 1 amino acid difference(s) from LCDR1, LCDR2 and LCDR3 region as set forth in SEQ ID NOs: 19-21, respectively; or (ii) the heavy chain variable region comprises HCDR1, HCDR2 and HCDR3 region as set forth in amino acid sequences of SEQ ID NOs: 22-24, or HCDR variants having 3, 2, or 1 amino acid difference(s) from HCDR1, HCDR2 and HCDR3 region as set forth in SEQ ID NOs: 22-24, respectively; and the light chain variable region comprises LCDR1, LCDR2 and LCDR3 region as set forth in amino acid sequences of SEQ ID NOs: 25-27, or LCDR variants having 3, 2, or 1 amino acid difference(s) from LCDR1, LCDR2 and LCDR3 region as set forth in SEQ ID NOs: 25-27, respectively; or (iii) the heavy chain variable region comprises HCDR1, HCDR2 and HCDR3 region as set forth in amino acid sequences of SEQ ID NOs: 28-30, or HCDR variants having 3, 2, or 1 amino acid difference(s) from HCDR1, HCDR2 and HCDR3 region as set forth in SEQ ID NOs: 28-30, respectively; and the light chain variable region comprises LCDR1. LCDR2 and LCDR3 region as set forth in amino acid sequences of SEQ ID NOs: 31-33, or LCDR variants having 3, 2, or 1 amino acid difference(s) from LCDR1, LCDR2 and LCDR3 region as set forth in SEQ ID NOs: 31-33, respectively; or (iv) the heavy chain variable region comprises HCDR1, HCDR2 and HCDR3 region as set forth in amino acid sequences of SEQ ID NOs: 34-36, or HCDR variants having 3, 2, or 1 amino acid difference(s) from HCDR1. HCDR2 and HCDR3 region as set forth in SEQ ID NOs: 34-36, respectively; and the light chain variable region comprises LCDR1, LCDR2 and LCDR3 region as set forth in amino acid sequences of SEQ ID NOs: 37-39, or LCDR variants having 3, 2, or 1 amino acid difference(s) from LCDR1, LCDR2 and LCDR3 region as set forth in SEQ ID NOs: 37-39, respectively; or (v) the heavy chain variable region comprises HCDR1, HCDR2 and HCDR3 region as set forth in amino acid sequences of SEQ ID NOs: 40-42, or HCDR variants having 3, 2, or 1 amino acid difference(s) from HCDR1, HCDR2 and HCDR3 region as set forth in SEQ ID NOs: 40-42, respectively; and the light chain variable region comprises LCDR1, LCDR2 and LCDR3 region as set forth in amino acid sequences of SEQ ID NOs: 43-45, or LCDR variants having 3, 2, or 1 amino acid difference(s) from LCDR1, LCDR2 and LCDR3 region as set forth in SEQ ID NOs: 43-45, respectively; or (vi) the heavy chain variable region comprises HCDR1, HCDR2 and HCDR3 region as set forth in amino acid sequences of SEQ ID NOs: 34-36, or HCDR variants having 3, 2, or 1 amino acid difference(s) from HCDR1, HCDR2 and HCDR3 region as set forth in SEQ ID NOs: 34, 82 and 36, respectively; and the light chain variable region comprises LCDR1. LCDR2 and LCDR3 region as set forth in amino acid sequences of SEQ ID NOs: 37-39, or LCDR variants having 3, 2, or 1 amino acid difference(s) from LCDR1, LCDR2 and LCDR3 region as set forth in SEQ ID NOs: 37-39, respectively.

In some embodiments, the variants of the monoclonal antibody or antigen-binding fragment CDRs (including 3 heavy chain CDRs and 3 light chain CDRs) having 3, 2 or 1 amino acid difference(s) are those that are obtained by affinity maturation methods.

In some embodiments, the monoclonal antibodies or antigen-binding fragments bind to IL-5 with an affinity (KD) of less than $10^{-8}$ M, less than $10^{-9}$ M, less than $10^{-10}$ M, or less than $10^{-11}$ M.

In some embodiments, the monoclonal antibody or antigen-binding fragment specifically binds to human IL-5, the monoclonal antibody comprises a heavy chain variable region and a light chain variable region, wherein:

(vii) the heavy chain variable region comprises HCDR1, HCDR2 and HCDR3 region as set forth in SEQ ID NOs: 16-18, and the light chain variable region comprises LCDR1, LCDR2 and LCDR3 region as set forth in SEQ ID NOs: 19-21; or (viii) the heavy chain variable region comprises HCDR1, HCDR2 and HCDR3 region as set forth in SEQ ID NOs: 22-24, and the light chain variable region comprises LCDR1, LCDR2 and LCDR3 region as set forth in SEQ ID NOs: 25-27; or (ix) the heavy chain variable region comprises HCDR1, HCDR2 and HCDR3 region as set forth in SEQ ID NOs: 28-30, and the light chain variable region comprises LCDR1, LCDR2 and LCDR3 region as set forth in SEQ ID NOs: 31-33; or (x) the heavy chain variable region comprises HCDR1, HCDR2 and HCDR3 region as set forth in SEQ ID NOs: 34-36, and the light chain variable region comprises LCDR1, LCDR2 and LCDR3 region as set forth in SEQ ID NOs: 37-39; or (xi) the heavy chain variable region comprises HCDR1, HCDR2 and HCDR3 region as set forth in SEQ ID NOs: 40-42, and the light chain variable region comprises LCDR1, LCDR2 and LCDR3 region as set forth in SEQ ID NOs: 43-45; or (xii) the heavy chain variable region comprises HCDR1, HCDR2 and HCDR3 region as set forth in SEQ ID NOs: 34, 82 and 36, and the light chain variable region comprises LCDR1, LCDR2 and LCDR3 region as set forth in SEQ ID NOs: 37-39.

In some embodiments, the monoclonal antibody is recombinant antibody.

In some embodiments, the monoclonal antibody is selected from the group consisting of murine antibody, chimeric antibody, recombinant antibody of a humanized antibody, or antigen-binding fragment thereof.

In some embodiments, the light and heavy chain FR region sequences on the humanized antibody light and heavy chain variable region are respectively derived from human germline light and heavy chain, or mutated sequences thereof.

In some embodiments of the monoclonal antibody or antigen-binding fragment thereof, the humanized antibody comprises a heavy chain variable region of SEQ ID NO: 49, 57, 63, 69 or 75, or a variant thereof; the variant has a 1-10 amino acid mutation(s) on the heavy chain variable region as set forth in SEQ ID NO: 49, 57, 63, 69 or 75.

In some embodiments of the monoclonal antibody or antigen-binding fragment thereof, the variant has 1-10 amino acid back mutations on the FR region of the heavy chain variable region as set forth in SEQ ID NO: 49, 57, 63, 69 or 75; preferably, the back mutation is selected from the group consisting of S49T, V93T and K98S, or a combination thereof on the heavy chain variable region of SEQ ID NO: 49, or the back mutation is selected from the group consisting of S49T, V93T and K98T, or a combination thereof on the heavy chain variable region of SEQ ID NO: 57, or the back mutation is selected from the group consisting of R38K, M48I, R67K, V68A, M70L, R72V, T74K and L83F, or a combination thereof on the heavy chain variable region of SEQ ID NO:63, or the back mutation is selected from the group consisting of F29I, R38K, V48I, R72A, T97F and N55V, or a combination thereof on the heavy chain variable region of SEQ ID NO:69, or the back mutation is selected from the group consisting of R38K, M48I, R67K, V68A, R72A, T74K, M81L, L83F and D89E, or a combination thereof on the heavy chain variable region of SEQ ID NO:75.

In some embodiments of the monoclonal antibody or antigen-binding fragment thereof, the humanized antibody comprises a heavy chain variable region of SEQ ID NO:50 or 51, or comprises a heavy chain variable region of SEQ ID NO: 58 or 59, or comprises a heavy chain variable region selected from any one of SEQ ID NO: 64, 65 and 66, or comprises a heavy chain variable region of SEQ ID NO:70 or 71, or comprises a heavy chain variable region selected from any one of SEQ ID NOs: 76 to 79.

In some embodiments of the monoclonal antibody or antigen-binding fragment thereof, the humanized antibody comprises a light chain variable region of SEQ ID NO: 46, 54, 60, 67 or 72 or variant thereof; the variant has 1-10 amino acid change(s) on the light chain variable region as set forth in SEQ ID NO: 46, 54, 60, 67 or 72.

In some embodiments of the monoclonal antibody or antigen-binding fragment thereof, the variant has 1-10 amino acid back mutation(s) on the FR region of the light chain variable region as set forth in SEQ ID NO: 46, 54, 60, 67 or 72; preferably, the back mutation is selected from the group consisting of A43S, L47V, G66R, T69S, F71Y and Y87F or a combination thereof on the light chain variable region of SEQ ID NO:46; or the back mutation is selected from the group consisting of A43S, L47M, F71Y and Y87F or a combination thereof on the light chain variable region of SEQ ID NO: 54; or the back mutation is selected from the group consisting of E1D, 12T, 157V, V84T and Y86F or a combination thereof on the light chain variable region of SEQ ID NO: 60; or the back mutation is selected from the group consisting of M4L, A42S. L45P and L46W or a combination thereof on the light chain variable region of SEQ ID NO: 67; or the back mutation is selected from the group consisting of A43S, I48V and F71Y or a combination thereof on the light chain variable region of SEQ ID NO:72.

In some embodiments of the monoclonal antibody or antigen-binding fragment thereof, the humanized antibody comprises a light chain variable region of SEQ ID NO: 47 or 48; or comprises a light chain variable region of SEQ ID NO: 55 or 56; or comprises a light chain variable region of SEQ ID NO: 61 or 62; or comprises a light chain variable region of SEQ ID NO: 68; or comprises a light chain variable region of SEQ ID NO: 73 or 74.

In some embodiments of the monoclonal antibody or antigen-binding fragment thereof, the humanized antibody comprises:

a heavy chain variable region selected from any one of SEQ ID NOs: 49-51 and a light chain variable region selected from any one of SEQ ID NOs: 46-48; or a heavy chain variable region selected from any one of SEQ ID NOs: 57-59 and a light chain variable region selected from any one of SEQ ID NOs: 54-56; or a heavy chain variable region selected from any one of SEQ ID NOs: 63-66 and a light chain variable region selected from any one of SEQ ID NOs: 60-62; or a heavy chain variable region selected from any one of SEQ ID NOs: 69-71 and a light chain variable region selected from any one of SEQ ID NOs: 67-68; or a heavy chain variable region selected from any one of SEQ ID NOs: 75-79 and a light chain variable region selected from any one of SEQ ID NOs: 72-74.

In some embodiments of the monoclonal antibody or antigen-binding fragment thereof, the antibody is a full-length antibody, further comprises a human antibody constant region, wherein the heavy chain constant region is preferably human IgG1, IgG2, IgG3, and IgG4 antibody heavy constant region. More preferably, the full-length antibody comprises a human antibody heavy chain constant region as set forth in SEQ ID NO: 52 and a human light chain constant region as set forth in SEQ ID NO:53.

In some embodiments, the antigen-binding fragment is selected from the group consisting of Fab, Fab', F(ab') 2, single-chain antibody (scFv), dimerized V region (diabody), disulfide-stabilized V region (dsFv) and a peptide comprising CDRs.

The present disclosure also provides an isolated monoclonal antibody or antigen-binding fragment thereof, which competes for binding to human IL-5 with the monoclonal antibody or antigen-binding fragment thereof described above.

The present disclosure also provides a pharmaceutical composition comprising a therapeutically effective amount of the monoclonal antibody or antigen-binding fragment thereof according to the present disclosure, and one or more pharmaceutically acceptable carriers, diluents, buffers or excipients. The amount of the monoclonal antibody or antigen-binding fragment thereof contained in the unit dose of the pharmaceutical composition is preferably from 0.1 to 2000 mg, more preferably from 1 to 1000 mg.

The present disclosure also provides an isolated nucleic acid molecule encoding the monoclonal antibody or antigen-binding fragment thereof according to the present disclosure.

The present disclosure also provides a recombinant vector comprising the nucleic acid molecule described above.

The present disclosure also provides a host cell transformed with the recombinant vector according to the present disclosure, the host cell being selected from the group consisting of prokaryotic cells and eukaryotic cells, preferably eukaryotic cells, more preferably mammalian cells.

The present disclosure also provides a method for producing the monoclonal antibody or antigen-binding fragment thereof according to the present disclosure, the method comprises cultivating the above host cell in a culture to form and accumulate the above monoclonal antibody or antigen-binding fragment thereof, and recovering the monoclonal antibody or antigen-binding fragment thereof from the culture.

The present disclosure also provides a method for detecting or determining human IL-5, the method comprises using the above monoclonal antibody or antigen-binding fragments thereof.

The present disclosure also provides an agent for detecting or determining human IL-5, which comprises the monoclonal antibody or antigen-binding fragment thereof according to any one of the above.

The present disclosure also provides a diagnostic agent for a disease associated with human IL-5, the diagnostic agent comprises the above monoclonal antibody or antigen-binding fragment thereof.

The present disclosure also provides a method for diagnosing a disease associated with human IL-5, the method comprises detecting or determining human IL-5 or IL-5 positive cells using the above monoclonal antibody or antigen-binding fragment thereof.

The present disclosure also provides use of the above monoclonal antibody or antigen-binding fragment thereof for the preparation of a diagnostic agent for a disease associated with human IL-5.

The present disclosure also provides a medicament for treating a disease associated with human IL-5, comprising the above monoclonal antibody or antigen-binding fragment thereof, or comprising the above pharmaceutical composition, or comprising the above nucleic acid molecule.

The present disclosure also provides a method of treating a disease associated with human IL-5, the method comprises administering to a subject a pharmaceutically effective amount of the above monoclonal antibody or antigen-binding fragment thereof, or a pharmaceutical composition comprising the same, or the above nucleic acid molecule to prevent or treat the disease associated with human IL-5.

The present disclosure also provides use of the above monoclonal antibody or antigen-binding fragment thereof, or the pharmaceutical composition comprising the same, or the above nucleic acid molecule for preparing a therapeutic agent for a disease associated with human IL-5.

The above disease or condition is preferably selected from the group consisting of asthma, malignant attack of asthma, chronic pneumonia, allergic rhinitis, allergic bronchopulmonary aspergillosis, eosinophilia, Churg-Strauss syndrome, atopic dermatitis, onchocerciasis dermatitis, intermittent angioedema, eosinophilic myalgia syndrome, eosinophilic gastroenteritis, helminth infection, Hodgkin's disease, nasal polyps, Loeffler's syndrome, urticaria, eosinophil hyperplastic bronchitis, nodular arteritis, sinusitis, eosinophilic esophagitis, allergic eosinophilic esophagitis, allergic conjunctivitis, onchocerciasis dermatitis, endometriosis and steroid dependent eosinophilic bronchitis.

The IL-5 monoclonal antibodies or antigen-binding fragments of the present disclosure have high specificity and high affinity with IL-5. The humanized antibodies have greatly reduced immunogenicity and completely retain specificity from the murine antibody and exhibit high affinity and excellent activities in vitro and in vivo.

The IL-5 monoclonal antibodies or antigen-binding fragments of the present disclosure have good selectivity for merely specifically recognizing IL5.

The IL-5 monoclonal antibodies or antigen-binding fragments of the present disclosure have good metabolic dynamic characteristics in rats, exhibit long half-life, and high bioavailability.

The IL-5 humanized antibody molecules of the present disclosure have good long-term stability, no obvious abnormal chemical modification, no obvious aggregation at high concentration, and high purity and thermal stability.

In addition to reducing the proliferation of eosinophils, the IL-5 monoclonal antibodies or antigen-binding fragments of the present disclosure have good properties in improving lung function.

DETAILED DESCRIPTION OF THE INVENTION

1. Terminology

Figure 1:
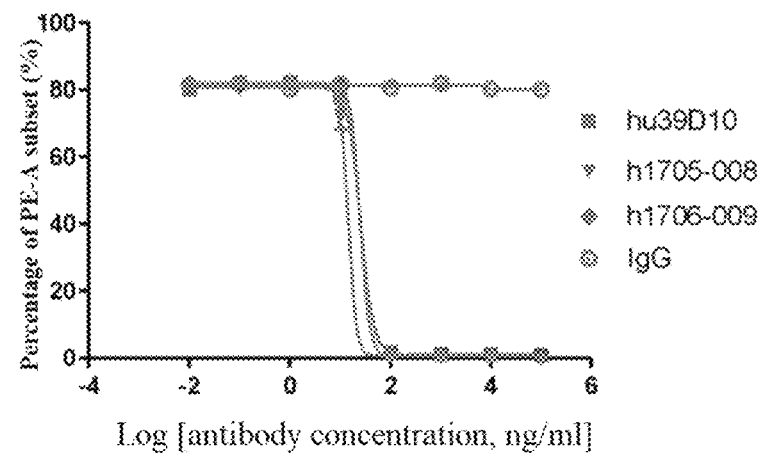
FIG. 1: IL-5 antibodies block the binding of IL-5 to IL-5 receptor in FACS experiment.

In order to more easily understand the present disclosure, certain technical and scientific terms are specifically defined below. Unless otherwise defined explicitly herein, all other technical and scientific terms used herein have the meaning commonly understood by one of ordinary skill in the art to which this disclosure belongs.

Three-letter codes and one-letter codes for amino acids used in the present disclosure are as described in J. biol. chem, 243, p 3558 (1968).

As used herein, "antibody" refers to immunoglobulin, a four-peptide chain structure connected together by disulfide bond between two identical heavy chains and two identical light chains. Different immunoglobulin heavy chain constant regions exhibit different amino acid compositions and rank orders, hence present different antigenicity. Accordingly, immunoglobulins can be divided into five types, or called immunoglobulin isotypes, namely IgM, IgD. IgG. IgA and IgE, with heavy chain μ, δ, γ, α and ε, respectively. According to its amino acid composition of hinge region and the number and location of heavy chain disulfide bonds, the same type of Ig can further be divided into different subtypes, for example, IgG can be divided into IgG1, IgG2, IgG3 and IgG4. Light chain can be divided into κ or λ chain, based on different constant region. Each of five types of Ig may has κ or λ chain.

In the present disclosure, the antibody light chain mentioned in present disclosure further comprises a light chain constant region, which comprises human or murine κ, λ chain or a variant thereof.

In the present disclosure, the antibody heavy chain mentioned in present disclosure further comprises a heavy chain constant region, which comprises human or murine IgG1, IgG 2, IgG 3, IgG 4 or a variant thereof.

About 110 amino acid sequences adjacent to the N-terminus of the antibody heavy and light chains are highly variable, known as variable region (Fv region); the rest of amino acid sequences close to the C-terminus are relatively stable, known as constant region. The variable region includes three hypervariable regions (HVRs) and four relatively conservative framework regions (FRs). The three hypervariable regions which determine the specificity of the antibody are also known as the complementarity determining regions (CDRs). Each light chain variable region (LCVR) and each heavy chain variable region (HCVR) consist of three CDR regions and four FR regions, with sequential order from the amino terminus to carboxyl terminus in the following order: FR1, CDR1, FR2, CDR2, FR3, CDR3, and FR4. The three CDR regions of the light chain refer to LCDR1, LCDR2, and LCDR3, and the three CDR regions of the heavy chain refer to HCDR1, HCDR2, and HCDR3. The number and position of CDR amino acid residues in the LCVR and HCVR regions of the antibody or antigen binding fragments herein comply with known Kabat numbering criteria (LCDR1-3, HCDR1-3).

The antibody of the present disclosure comprises murine antibody, chimeric antibody and humanized antibody, preferably is humanized antibody.

The term "murine antibody" in the present disclosure refers to anti-human IL-5 monoclonal antibody prepared according to the knowledge and skills of the field. During the preparation, test subject may be injected with IL-5 antigen, and then a hybridoma expressing the antibody which possesses desired sequence or functional characteristics is isolated. In a preferred embodiment of the present disclosure, the murine IL-5 antibody or antigen binding fragment thereof further comprises light chain constant region of murine κ, λ chain or a variant thereof, or further comprises heavy chain constant region of murine IgG1, IgG2, IgG3 or IgG4, or a variant thereof.

The term "chimeric antibody", is an antibody by fusing the variable region of murine antibody with the constant region of human antibody, and the chimeric antibody can alleviate the murine antibody-induced immune response. To establish a chimeric antibody, a hybridoma secreting specific murine monoclonal antibody may be established and a variable region gene is cloned from the murine hybridoma. Then a desired constant region gene of human antibody can be cloned, and connected with a variable region gene of murine to form a chimeric gene which can be subsequently inserted into an expression vector. Finally the chimeric antibody molecule will be expressed in the eukaryotic or prokaryotic system. In a preferred embodiment of the present disclosure, the light chain of the IL-5 chimeric antibody further comprises a light chain constant region derived from human κ, λ chain or a variant thereof. The heavy chain of IL-5 chimeric antibody further comprises a heave chain constant region derived from human IgG1, IgG2, IgG3, IgG4 or a variant thereof, preferably comprises a heavy chain constant region derived from human IgG1, IgG2 or IgG4, or comprises a heavy chain constant region variant of human IgG1, IgG2 or IgG4 with amino acid mutation(s), such as YTE mutation(s) or back-mutation(s).

The term "humanized antibody", refers to an antibody generated by grafting murine CDR sequences into human antibody variable region framework, i.e., an antibody produced in different types of human germline antibody framework sequences. Humanized antibody can overcome heterologous responses induced by large number of murine protein components carried by chimeric antibody. Such framework sequences can be obtained from public DNA database covering germline antibody gene sequences or published references. For example, germline DNA sequences of human heavy and light chain variable region genes can be found in "VBase" human germline sequence database (available on web www.mrccpe.com.ac.uk/vbase), as well as in Kabat, E A, et al. 1991 Sequences of Proteins of Immunological Interest, 5th Ed. To avoid a decrease in activity caused by the decreased immunogenicity, the framework sequences in the variable region of human antibody may be subjected to minimal reverse mutations or back mutations to maintain the activity. The humanized antibody of the present disclosure also comprises humanized antibody on which CDR affinity maturation is performed by phage display. In a preferred embodiment of the present disclosure, the CDR sequence of the IL-5 humanized antibody is selected from the group consisting of SEQ ID NOs: 16-21, 22-27, 28-33, 34-39 and 40-45. The human antibody variable region framework is designed and selected, wherein the FR region sequence on the antibody heavy chain variable region is derived from the human germline heavy chain sequence and the human germline light chain sequence. To avoid a decrease in activity caused by the decreased immunogenicity, the human antibody variable region may be subjected to minimal reverse mutations (back mutations, that is, the FR region amino acid residues derived from human antibody are replaced with amino acid residues corresponding to the original antibody) to maintain the activity.

The graft of CDR can result in the decrease of the affinity of the resulting IL-5 antibody or antigen binding fragment thereof to the antigen due to the change in the framework residues contacted with the antigen. Such interactions may be the result of highly somatic mutations. Therefore, it may still be necessary to transfer the donor framework amino acids to the humanized antibody framework. The amino acid residues derived from non-human IL-5 antibody or antigen binding fragment thereof, that are involved in antigen binding, can be identified by checking the sequence and structure of murine monoclonal antibody variable region. The amino acid residues in donor CDR framework that are different from those in the germ lines can be considered to be related. If it is not possible to determine the most closely related germ line, the sequence can be compared with the common sequence shared among the subtypes or with the common sequence of murine sequences having high similarity percentage. Rare framework residues are thought to be the result of a high mutation in somatic cells, which play an important role in binding.

As used herein, "antigen-binding fragment" or "functional fragment" refers to one or more fragment(s) of antibody retaining the binding ability to the antigen (e.g. IL-5). It has been shown that fragments of full-length antibody can be used to achieve function of binding with an antigen. The examples of binding fragments in the term "antigen binding fragment" include (i) Fab fragment, a monovalent fragment composed of VL, VH, CL and CH1 domain; (ii) F(ab')$_2$ fragment, a bivalent fragment comprising two Fab fragments linked by a disulphide bond in hinge region; (iii) Fd fragment, consisting of VH and CH1 domains; (iv) Fv fragment, consisting of VH and VL domains of one-arm antibody; (v) single domain or dAb fragment (Ward et al. (1989) Nature341:544-546) composed of VH domain; and (vi) a separate complementary determining region (CDR) and (vii) a combination of two or more separate CDRs optionally linked by a synthetic linker. In addition, although the VL domain and VH domain of the Fv fragment are encoded by two separate genes, they can be linked by a synthetic linker by using recombinant methods, thereby generating a single protein chain of a monovalent molecular formed by pairing the VL and VH domain (referred to as single chain Fv (scFv); see, e.g., Bird et al. (1988); Science 242: 423-426 and Huston et al (1988) Proc. Natl. Acad. Sci USA85:5879-5883). This single chain antibody is also intended to be included in the term "antigen binding fragment" of the antibody. Such antibody fragments are obtained using conventional techniques known in the field, and screened for functional fragments by using the same method as that for an intact antibody. Antigen binding portions can be produced by recombinant DNA technology or by enzymatic or chemical disruption of an intact immunoglobulin. Antibodies can be in the form of different isotypes, e.g., IgG (e.g., IgG1, IgG2, IgG3 or IgG4 subtype), IgA1, IgA2, IgD, IgE or IgM antibody.

The antigen-binding fragment in the present disclosure includes Fab, F(ab')2, Fab', single-chain antibody(scFv), dimerized V region (diabody), disulfide stabilized V region (dsFv) and CDR-containing peptide.

Fab is an antibody fragment obtained by treating an IgG antibody molecule with a papain (which cleaves the amino acid residue at position 224 of the H chain). The Fab fragment has a molecular weight of about 50,000 and has antigen binding activity, in which about a half of the N-terminal side of H chain and the entire L chain are bound together through a disulfide bond.

The Fab of the present disclosure can be produced by treating the monoclonal antibody of the present invention which specifically recognizes human IL-5 and binds to the amino acid sequence of extracellular region or three-dimensional structure thereof with papain. Also, the Fab can be produced by inserting DNA encoding Fab of the antibody into a prokaryotic expression vector or eukaryotic expression vector and introducing the vector into a prokaryote or eukaryote to express the Fab.

F(ab')2 is an antibody fragment having a molecular weight of about 100.000 and having antigen binding activity and comprising two Fab regions which are bound at the hinge position, F(ab')2 is obtained by digesting the downstream part of the two disulfide bonds in the hinge region of IgG with pepsin.

The F(ab')2 of the present disclosure can be produced by treating the monoclonal antibody of the present disclosure which specifically recognizes human IL-5 and binds to the amino acid sequence of extracellular region or three-dimensional structure thereof with pepsin. Also, the F(ab')2 can be produced by binding the Fab' described below via a thioether bond or a disulfide bond.

Fab' is an antibody fragment having a molecular weight of about 50,000 and having antigen binding activity. Fab' is obtained by cleaving a disulfide bond at the hinge region of the above F(ab')2. The Fab' of the present disclosure can be produced by treating the F(ab')2 of the present invention which specifically recognizes IL-5 and binds to the amino acid sequence of extracellular region or three-dimensional structure thereof with a reducing agent, such as dithiothreitol.

Also, the Fab' can be produced by inserting DNA encoding Fab' fragment of the antibody into a prokaryotic expression vector or eukaryotic expression vector and introducing the vector into a prokaryote or eukaryote to express the Fab'.

The term "single chain antibody", "single chain Fv" or "scFv" refers to a molecule comprising an antibody heavy chain variable domain (or region; VH) and an antibody light chain variable domain (or region; VL) connected by a linker. Such scFv molecules have the general structure of NH$_2$-VL-linker-VH—COOH or NH$_2$—VH-linker-VL-COOH. A suitable linker in the prior art consists of repeated GGGGS amino acid sequence or variant thereof, for example, using a variant with 1-4 repeats (Holliger et al. (1993), Proc. Natl. Acad. Sci. USA 90:6444-6448). Other linkers that can be used for the present disclosure are described by Alfthan et al. (1995), Protein Eng. 8:725-731. Choi et al.(2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol.

The scFv of the present disclosure can be produced by the following steps: obtaining cDNAs encoding VH and VL of the monoclonal antibody of the present disclosure which specifically recognizes human IL-5 and binds to the amino acid sequence of extracellular region or three-dimensional structure thereof, constructing DNA encoding scFv, inserting the DNA into a prokaryotic expression vector or eukaryotic expression vector, and then introducing the expression vector into a prokaryote or eukaryote to express the scFv.

A diabody is an antibody fragment wherein the scFv is dimerized, and is an antibody fragment having divalent antigen binding activity. In the divalent antigen binding activity, two antigens may be the same or different.

The diabody of the present disclosure can be produced by the following steps, obtaining cDNAs encoding VH and VL of the monoclonal antibody of the present disclosure which specifically recognizes human IL-5 and binds to the amino acid sequence of extracellular region or three-dimensional structure thereof, constructing DNA encoding scFv so that the length of the linker peptide is 8 or less amino acid residues, inserting the DNA into a prokaryotic expression vector or eukaryotic expression vector, and then introducing the expression vector into a prokaryote or eukaryote to express the diabody.

A dsFv is obtained by substituting one amino acid residue in each of VH and VL with a cysteine residue, and then connecting the substituted polypeptides via a disulfide bond between the two cysteine residues. The amino acid residue to be substituted with a cysteine residue can be selected based on three-dimensional structure prediction of the antibody in accordance with known methods (Protein Engineering, 7, 697 (1994)).

The dsFv of the present disclosure can be produced by the following steps: obtaining cDNAs encoding VH and VL of the monoclonal antibody of the present disclosure which specifically recognizes human IL-5 and binds to the amino acid sequence of extracellular region or three-dimensional structure thereof, constructing DNA encoding dsFv, inserting the DNA into a prokaryotic expression vector or eukaryotic expression vector, and then introducing the expression vector into a prokaryote or eukaryote to express the dsFv.

A CDR-containing peptide is constructed by one or more region(s) of CDRs of VH and VL. Peptides comprising several CDRs can be joined directly or via a suitable peptide linker.

The CDR-containing peptide of the present disclosure can be produced by the steps of: constructing a DNA encoding the CDRs of VH and VL of the monoclonal antibody of the present disclosure which specifically recognizes human IL-5 and binds to the amino acid sequence of extracellular region amino acid sequence or three-dimensional structure thereof, inserting the DNA into a prokaryotic expression vector or eukaryotic expression vector, and then introducing the expression vector into a prokaryote or eukaryote to express the peptide. The CDR-containing peptide can also be produced by a chemical synthesis method such as Fmoc method or tBoc method.

The term "antibody framework" as used herein refers to part of the variable domain, either VL or VH, which serves as a scaffold for the antigen binding loops (CDRs) of this variable domain. In essence it is the variable domain without the CDRs.

The term "amino acid difference" refers to differences on one or more amino acid position(s) along the length of a polypeptide fragment between a polypeptide and a variant thereof, wherein the variant may be obtained by replacing, inserting or deleting one or more amino acid(s) on the polypeptide.

The term "epitope" or "antigenic determinant" refers to a site on an antigen to which an immunoglobulin or antibody specifically binds (e.g., a specific site on the IL-5 molecule). Epitopes typically include at least 3, 4, 5, 6, 7, 8, 9, 10, 11, 12, 13, 14 or 15 consecutive or non-consecutive amino acids in a unique tertiary conformation. See, for example, Epitope Mapping Protocols in Methods in Molecular Biology. Vol. 66, ed. G. E. Morris (1996).

The term "specifically bind to", "selectively bind to", "selectively binds to" or "specifically binds to" refers to the binding of an antibody to a predetermined epitope on an antigen. Typically, the antibody binds with an affinity (KD) of less than about $10^{-8}$ M, for example, less than about $10^{-9}$ M, $10^{-10}$ M or $10^{-11}$ M or even less.

The term "KD" refers to the dissociation equilibrium constant for particular antibody-antigen interaction. Typically, the antibody of the present disclosure binds to IL-5 with a dissociation equilibrium constant (KD) of less than about $10^{-7}$ M, such as less than about $10^{-8}$ M, $10^{-9}$ M or $10^{-10}$ M or even less, for example, as determined using surface plasmon resonance (SPR) techniques in a BIACORE instrument.

When the term "competition" is used in the context of antigen binding proteins (e.g., neutralizing antigen binding proteins or neutralizing antibodies) that compete for the same epitope, it means that competition occurs among the antigen binding proteins, which is determined by the following assays: an antigen binding protein to be tested (e.g., an antibody or immunologically functional fragment thereof) prevents or inhibits (e.g., reduces) the specific binding between a reference antigen binding protein (e.g., a ligand or reference antibody) and a common antigen (e.g., an IL-5 antigen or fragment thereof). Numerous types of competitive binding assays are available to determine whether an antigen binding protein competes with another. These assays are, for example, solid phase direct or indirect radioimmunoassay (RIA), solid phase direct or indirect enzyme immunoassay (EIA), Sandwich competition assay (see, e.g., Stahli et al, 1983, Methods in Enzymology 9: 242-253); solid phase direct biotin-avidin EIA (see, e.g., Kirkland et al, 1986, J. Immunol. 137: 3614-3619), solid phase direct labeling assay, solid phase direct labeling sandwich assay (see, e.g., Harlow and Lane, 1988, Antibodies, A Laboratory Manual, Cold Spring Harbor Press); solid phase direct labeling RIA with 1-125 label (see, e.g., Morel et al, 1988, Molec. Immunol. 25: 7-15); solid phase direct biotin-avidin EIA (see, e.g., Cheung, et al, 1990, Virology 176: 546-552); and direct labeling RIA (Moldenhauer et al, 1990, Scand. J. Immunol. 32: 77-82). Typically, the assay involves the use of a purified antigen (either on a solid surface or on a cell surface) capable of binding to both an unlabeled antigen binding protein to be tested and a labeled reference antigen binding protein. Competitive inhibition is determined by measuring the amount of label bound to the solid surface or to the cell in the presence of the antigen binding protein to be tested. Usually, the antigen binding protein to be tested is present in excess. Antigen binding proteins identified by competitive assay (competing with the antigen binding protein) includes: antigen binding proteins that bind to the same epitope as the reference antigen binding protein; and antigen binding proteins that bind to an epitope that is sufficiently close to the epitope to which the reference antigen binding protein binds, where the two epitopes spatially interfere with each other to hinder the binding. Additional details regarding methods for determining competitive binding are provided in the Examples herein. Typically, when a competing antigen binding protein is present in excess, it will inhibit (e.g., reduce) at least 40-45%, 45-50%, 50-55%, 55-60%, 60-65%, 65-70%, 70-75% or 75% or even more of the specific binding between the reference antigen binding protein and the common antigen. In some cases, the binding is inhibited by at least 80-85%, 85-90%, 90-95%, 95-970/%, or 97% or even more.

The term "nucleic acid molecule," as used herein refers to DNA molecules and RNA molecules. A nucleic acid molecule may be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence.

The term "vector" refers to a nucleic acid molecule capable of transporting another nucleic acid to which it has been linked. In one embodiment, the vector is a "plasmid." which refers to a circular double stranded DNA loop into which additional DNA segments may be ligated. In another embodiment, the vector is a viral vector, wherein additional DNA segments may be ligated into the viral genome. The vectors disclosed herein are capable of self-replicating in the host cell into which they are introduced (e.g., bacterial vectors having a bacterial replication origin and episomal mammalian vectors), or may be integrated into the genome of a host cell upon introduction into the host cell, and thereby are replicated along with the host genome (e.g., non-episomal mammalian vectors).

Methods for producing and purifying antibodies and antigen-binding fragments are well known in the art and can be found, for example, in Antibodies, A Laboratory Manual, Cold Spring Harbor Laboratory Press, chapters 5-8 and 15. For example, mice can be immunized with human IL-5 or fragments thereof, and the resulting antibodies can then be renatured, purified, and sequenced for amino acid sequences by using conventional methods well known in the art. Antigen-binding fragments can also be prepared by conventional methods. The antibodies or antigen binding fragments of the present disclosure are engineered to contain one or more human FR region(s) on CDRs derived from a non-human antibody. Human FR germline sequences can be obtained by aligning human antibody variable germline gene database and MOE software from ImMunoGeneTics (IMGT) via their website http://imgt.cines.fr, or from The Immunoglobulin Facts Book, 2001, ISBN 012441351.

The term "host cell" refers to a cell into which the expression vector has been introduced. Host cells may include microbial (e.g. bacterial), plant or animal cells. Bacteria that are susceptible to be transformed include members of enterobacteriaceae, such as *Escherichia coli* or *Salmonella* strains; Bacillaceae such as *Bacillus subtilis*; Pneumococcus; *Streptococcus* and *Haemophilus influenzae*. Suitable microorganisms include *Saccharomyces cerevisiae* and *Pichia pastoris*. Suitable animal host cell lines include, but are not limited to CHO (Chinese hamster ovary cell line), HEK cells (as non-limiting examples, HEK293E cells) and NS0 cells.

The engineered antibodies or antigen binding fragments of the present disclosure may be prepared and purified using known methods. For example, cDNA sequence encoding a heavy chain and a light chain may be cloned and engineered into a GS expression vector. The recombinant immunoglobulin expression vector may then be stably transfected into CHO cells. As a more recommended method well known in the art, mammalian expression systems will result in glycosylation of the antibody, typically at highly conserved N-terminal sites in the Fc region. Stable clones may be verified for expression of an antibody specifically binding to human IL-5. Positive clones may be expanded in serum-free culture medium in bioreactors for antibody production. Culture medium, into which an antibody has been secreted, may be purified by conventional techniques. For example, purification can be performed on Protein A or G Sepharose FF column that has been equilibrated with an adjusted buffer. The column is washed to remove nonspecific binding components, and then the bound antibody is eluted by pH gradient and antibody fractions are detected by SDS-PAGE, and then collected. The antibodies may be filtered and concentrated using common techniques. Soluble mixtures and polymers may be removed by common techniques, such as size exclusion or ion exchange. The resulting product is then immediately frozen, for example at −70° C., or may be lyophilized.

"Administration", "administering" or "treatment," as it applies to an animal, human, subject, cell, tissue, organ, or biological fluid, refers to contacting an exogenous pharmaceutical, therapeutic, diagnostic agent, or composition with the animal, human, subject, cell, tissue, organ, or biological fluid. "Administration", "administering" or "treatment" can refer, e.g., to therapeutic, pharmacokinetic, diagnostic, research, and experimental methods. Treatment of a cell encompasses contacting a reagent with the cell, as well as contacting a reagent with a fluid, where the fluid is in contact with the cell. "Administration", "administering" or "treatment" also means in vitro and ex vivo treatments of a cell, with a reagent, diagnostic, binding composition, or with another cell. "Treatment," as it applies to a human, veterinary, or research subject, refers to therapeutic treatment, prophylactic or preventative measures, to research and diagnostic applications.

"Treat" means administration of a therapeutic agent, such as a composition containing any of antibodies or fragment thereof of the present disclosure, internally or externally to a patient having one or more disease symptom(s) for which the agent has known therapeutic activity. Typically, the agent is administered in an amount effective to alleviate one or more disease symptom(s) in the patient or population to be treated, by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present disclosure (e.g., a treatment method or article of manufacture) may not be effective in alleviating the target disease symptom(s) in every patient, it should alleviate the target disease symptom(s) in a statistically significant number of patients as determined by any statistical test known in the art such as the Student's t-test, the chi-square test, the U-test according to Mann and Whitney, the Kruskal-Wallis test (H-test), Jonckheere-Terpstra-test and the Wilcoxon-test.

"Conservative modification" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitution in non-essential regions of a polypeptide does not substantially alter biological activity (see, e.g., Watson et al. (1987) Molecular Biology of the Gene. The Benjamin/Cummings Pub. Co., p. 224 (4th Ed.)). In addition, substitutions with structurally or functionally similar amino acids are less likely to disrupt biological activity.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health condition of the patient, the route and dose of administration and the severity of side effects. An effective amount can be the maximal dose or dosing protocol that avoids significant side effects or toxic effects.

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptide sequences. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions to be compared and then multiplied by 100. For example, if 6 out of 10 positions in two sequences are matched or homologous when the sequences are optimally aligned, then the two sequences have 60% homology; if 95 out of 100 positions in two sequences are matched or homologous, then the two sequences have 95% homology. Generally, the comparison is performed when two sequences are aligned to give maximum percent homology.

As used herein, the expressions "cell," "cell line," and "cell culture" are used interchangeably and all such designations include progeny. Thus, the words "transformants" and "transformed cells" include the primary subject cells and cultures derived therefrom regardless of the number of passages. It should be also understood that all progeny may not be precisely identical in DNA content, due to deliberate or inadvertent mutations. Mutant progeny that have the same function or biological activity as screened in the originally transformed cells are included. Where distinct designations are intended, it will be clearly understood from the context.

As used herein, "polymerase chain reaction" or "PCR" refers to a procedure or technique in which minute amounts of a specific portion of nucleic acid, RNA and/or DNA, are amplified as described in, e.g., U.S. Pat. No. 4,683,195. Generally, sequence information about the ends of the region of interest or beyond the region of interest needs to be available, such that oligonucleotide primers can be designed; these primers will be identical or similar in sequence to opposite strands of the template to be amplified. The 5' terminal nucleotides of the two primers are in consistence with the ends of the material to be amplified. PCR can be used to amplify specific RNA sequences, specific DNA sequences from total genomic DNA, and cDNA transcribed from total cellular RNA, bacteriophage or plasmid sequences, etc. See generally Mullis et al. (1987) Cold Spring Harbor Symp. Ouant. Biol. 51:263; Erlich, ed., (1989) PCR TECHNOLOGY (Stockton Press, N.Y.). The PCR test used in the present disclosure is considered to be one, but not the only, example of polymerase reaction method for amplifying a nucleic acid test sample. The method comprises the use of known nucleic acid sequences as primers and nucleic acid polymerase to amplify or generate a specific portion of nucleic acid.

"Optional" or "optionally" means that the event or situation that follows may but does not necessarily occur, and the description includes the instances in which the event or circumstance does or does not occur. For example, "optionally contains 1-3 antibody heavy chain variable regions" means the antibody heavy chain variable region with specific sequence can be, but need not be, present.

"Pharmaceutical composition" refers to a mixture containing one or more compound(s) according to the present disclosure or a physiologically/pharmaceutically acceptable salt or produg thereof and other chemical components, such as physiologically/pharmaceutically acceptable carriers and excipients. The pharmaceutical composition aims at promoting the administration to an organism, facilitating the absorption of the active ingredient and thereby exerting a biological effect.

Furthermore, the present disclosure includes an agent for treating diseases associated with IL-5, and the agent comprises the monoclonal antibody of the present disclosure or antibody fragment thereof as an active ingredient.

There is not limitation for the diseases associated with IL-5, as long as they are associated with IL-5. For example, the therapeutic responses induced by the molecules of present disclosure can be generated by binding to human IL-5 and consequently repressing or inhibiting eosinophil-induced stimulation. Thus, when being in preparations and formulations suitable for therapeutic applications, the molecules of the present disclosure are very useful for individuals who are suffering from allergic and/or atopic responses or responses associated with eosinophils, for example, but are not limited to, asthma, asthma exacerbation, malignant attack of asthma, chronic pneumonia, allergic rhinitis, perennial allergic rhinitis, allergic bronchopulmonary aspergillosis, eosinophilia, Churg-Strauss syndrome, atopic dermatitis, onchocerciasis dermatitis, intermittent angioedema, eosinophilic myalgia syndrome, eosinophilic gastroenteritis, helminth infection, Hodgkin's disease, nasal polyps, Loeffler's syndrome, urticaria, eosinophil hyperplastic bronchitis, nodular arteritis, sinusitis, eosinophilic esophagitis, allergic eosinophilic esophagitis, allergic conjunctivitis, onchocerciasis dermatitis, endometriosis and steroid dependent eosinophilic bronchitis, and the like. In a preferred embodiment, such treatment inhibits or reduces the infiltrating-eosinophils in lung tissue. The antibodies or fragment thereof may be administered from three times a day to once every six months, and may be intravenously, subcutaneously, intramuscularly, parenterally or topically administered.

Furthermore, the present disclosure relates to an immunodetection or immunoassay method of IL-5, reagents for immunodetection or immunoassay of IL-5, an immunodetection or immunoassay of cells expressing IL-5, and a diagnostic agent for diagnosing a disease associated with IL-5, which comprises the monoclonal antibody or antibody fragment of the present disclosure specifically recognizing human IL-5 and binding to the amino acid sequence of the extracellular region or the three-dimensional structure thereof as an active ingredient.

In the present disclosure, the method for detecting or determining the amount of IL-5 may be any method known in the art. For example, it includes immunodetection or immunoassay.

The immunodetection or immunoassay is a method for detecting or determining the amount of an antibody or of an antigen by using a labeled antigen or antibody. Examples of immunodetection or immunoassay include radioactive substance labeling immunological antibody method (RIA), enzyme immunoassay (EIA or ELISA), fluorescent immunoassay (FIA), luminescent immunoassay, Western Blotting, physicochemical assays, and the like.

The above diseases associated with IL-5 can be diagnosed by detecting or determining the cells expressing IL-5 with the monoclonal antibody or antibody fragment of the present disclosure.

In order to detect cells expressing the polypeptide, a known immunoassay can be used, preferably, immunoprecipitation, fluorescent cell staining, immunohistochemical staining, and the like is used. Further, a fluorescent antibody staining method with FMAT8100HTS system (Applied Biosystem), and the like can be used.

In the present disclosure, a living sample used for detecting or determining IL-5 is not particularly limited, as long as it is likely to contain cells expressing IL-5, for example, tissue cells, blood, plasma, serum, pancreatic fluid, urine, feces, tissue fluid or culture medium can be used.

The diagnostic agent comprising the monoclonal antibody or antibody fragment thereof of the present disclosure may further comprise an agent for performing antigen-antibody reaction or an agent for detecting the reaction, depending on a desired diagnostic method. The agent for performing antigen-antibody reaction includes such as buffer and salts. The agent for detecting the reaction includes reagents commonly used in immunodetection or immunoassay method, for example, such as a labeled secondary antibody recognizing the monoclonal antibody, antibody fragment thereof or conjugate comprising the same, and a substrate corresponding to the labels.

2. Examples and Test Examples

The following examples are provided to further describe the present disclosure, but are not intended to limit the scope of the disclosure. Experimental methods for which the specific conditions are not specifically indicated are generally carried out according to conventional conditions, see Molecular Cloning, Laboratory Manual of antibody technology, Cold Spring Harbor Laboratory; or according to the conditions recommended by the manufacturer of materials or products. Reagents for which the sources are not specifically indicated are commercially available reagents.

Example 1. Preparation of IL-5 Antigens and Proteins for Detection

Design and Expression of IL-5 antigen

Sequences encoding His-tagged human IL-5, Rhesus monkey IL-5, mouse IL-5, rat IL-5, or human IL-5Rα receptor extracellular domain fused to human IgG1-Fc fragment were inserted into the phr vector, to construct expression plasmids, which were then transfected into HEK293. On day 6 after transfection, samples were centrifuged at 4500 rpm for 10 min and cell supernatants were collected. The supernatant containing recombinant IL-5 or IL-5α receptor protein was purified by using nickel column, and the recombinant human IL-5-Fc fusion protein was purified by using Protein A affinity chromatography column. The purified protein can be used in the following examples. The protein sequences of the antigen are shown as follows:

1. Human IL-5 amino acid sequence with his tag (rhIL-5-his)
SEQ ID NO: 1
MRMLLHLSLLALGAAYVYAIPTEIPTSALVKETLALLSTHRTLLIANETLR

IPVPVHKNHQLCTEEIFQGIGTLESQTVQGGTVERLFKNLSLIKKYIDGQK

KKCGEERRRVNQFLDYLQEFLGVMNTEWIIES*HHHHHH*
Note:
The italic text shows His6-tag

2. Cynomolgus monkey IL-5 amino acid sequence with his tag
SEQ ID NO: 2
MRMLLHLSLLALGAAYVYAIPTEIPASALVKETLALLSTHRTLLIANETLR

IPVPVHKNHQLCTEEIFQGIFTLESQTVQGGTVERLFKNLSLIKKYIGGQK

KKCGEERRRVNQFLDYLQEFLGVMNTEWIIES*HHHHHH*

-continued
Note:
The italic text shows His6-tag.

3. Mouse IL-5 amino acid sequence with his tag
SEQ NO NO: 3
MEIPMSTVVKETLTQLSAHRALLTSNETMRLPVPTHKNHQLCIGEIFQGLD

ILKNQTVRGGTVEMLFQNLSLIKKYIDRQKEKCGEERRRTRQFLDYLQEFL

GVMSTEWAMEG*HHHHHH*
Note:
The italic text shows His6-tag.

4. Rat IL-5 amino acid sequence with his tag
SEQ ID NO: 4
MEIPMSTVVKETLIQLSTHRALLTSNETMRLPVPTHKNHQLCIGEIFQGLD

ILKNQTVRGGTVEILFQNLSLIKKYIDGQKEKCGEERRKTRHFLDYLQEFL

GVMSTEWAMEV*HHHHHH*
Note:
The italic text shows His6-tag.

5. Amino acid sequence of human IL-5α receptor fused to human Fc fragment
SEQ ID NO: 5
DLLPDEKISLLPPVNFTIKVTGLAQVLLQWKPNPDQEQRNVNLEYQVKINA

PKEDDYETRITESKCVTILHKGFSASVRTILQNDHSLLASSWASAELHAPP

GSPGTSIVNLTCTTNTTEDNYSRLRSYQVSLHCTWLVGTDAPEDTQYFLYY

RYGSWTEECQEYSKDTLGRNIACWFPRTFILSKGRDWLAVLVNGSSKHSAI

RPFDQLFALHAIDQINPPLNVTAEIEGTRLSIQWEKPVSAFPIHCFDYEVK

IHNTRNGYLQIEKLMTNAFISIIDDLSKYDVQVRAAVSSMCREAGLWSEWS

QPIYVGNDEHKPLREWI EGRMD*EPKSCDKTHTCPPCPAPELLGGPSVFLFP*

*PKPKDTLMISRTPEVTCVVVDVSHEDPEVKFNWYYDGVEVHNAKTKPREEQ*

*YNSTYRVVSVLTVLHQDWLNGKEYKCKVSNKALPAPIEKTISKAKGQPREP*

*QVYTLPPSRDELTKNQVSLTCLVKGFYPSDIAVEWESNGQPENNYKTTPPV*

*LDSDGSFFLYSKLTVDKSRWQQGNVFSCSVMHEALHNHYTQKSLSLSPGK*
Note:
The italic text shows human Fc tag.

Example 2: Construction and Identification of Recombinant IL-5α Receptor and IL-5α/β Receptor Cell Lines To screen for functional antibodies, the present disclosure construct a CHO—S/IL-5α cell line expressing IL-5α, and a CHO-S/IL-5α/IL-5β cell line expressing both IL-5α and IL-5β.

Specifically, full-length human IL-5α gene (Q01344) was cloned into a mammalian cell expression vector, pTargeT, and the linearized plasmid was transfected into CHO-S cells via electroporation. Screening was performed under G418 for 2 weeks, followed by two rounds of limiting dilutions. The IL-5α gene expressed on cell surface was detected by FACS, CHO-S/IL-5α cell lines with high expression level of IL-5α were selected and transfected into the linearized pcDNA3.1-IL-5β via electroporation. Screening was performed with G418 and zeocin for 2 weeks, followed by two rounds of limiting dilutions. The IL-5α and IL-5β gene expressed on the cell surface were detected by FACS, and CHO-S/IL-5α/IL-5β cell lines with high expression of IL-5α and IL-5β were selected.

Example 3: Preparation of Anti-Human IL-5 Murine Monoclonal Antibody

Two groups of Balb/c mice (5 mice/group) and four groups of SJL mice (5 mice/group) were immunized with recombinant protein rhIL-5-his and Freund's adjuvant CFA (Sigma. Lot #SLBQ1109V); or with IFA (Sigma, Lot #SLBJ2845V) at two dosages of 100 g/50 g/50 g (high-dose group) and of 25 g/12.5 g/12.5 g(low-dose group), respectively. The specific immune response to IL-5 was determined by detecting serum titer by ELISA, Ligand-Receptor Blocking assay and TF-1 Proliferation Inhibition Assay. Mice with better specific immune response were selected, sacrificed, spleen cells were collected and fused with myeloma cells.

Primary screening was performed by using an ELISA binding assay against human IL-5. The hybridoma cells were transferred into 24-well plates, and the supernatants were rescreened by ELISA binding assay against human, cynomolgus, or mouse IL-5 by ELISA-based blocking assay against IL-5 receptor and by TF-1 proliferation inhibition assay. After such screening, the obtained positive clones were subjected to two rounds of subcloning to obtain hybridoma clones for antibody production. The obtained antibodies were purified by affinity chromatography.

The purified antibodies were subjected to the following tests: SEC-HPLC, detection of endotoxin content, Biacore assay for affinity to various IL-5, FACS-based blocking assay against IL-5 receptor, and TF-1 proliferation inhibition assay, adhesion test of eosinophils, and evaluation of efficacy on mouse asthma model and in vivo guinea pig neutralization model. Monoclonal hybridoma cell lines mAb1705, mAb1706, mAb1780, mAb1773 and mAb1779 were selected for their excellent activities in vitro and in vivo.

The sequences were cloned from positive hybridoma as follows. The hybridoma cells in logarithmic growth phase were collected, RNAs were extracted with Trizol (Invitrogen, Cat No. 15596-018) according to the manufacturer's instruction or kit, and reverse transcription was performed with PrimeScript™ Reverse Transcriptase kit (Takara. Cat No. 2680A). The cDNAs obtained by reverse transcription were subjected to PCR amplification using mouse Ig-Primer Set (Novagen, TB326 Rev. B 0503) and the resulting products were sequenced. The amino acid sequences corresponding to DNA sequences of mAb1705, mAb1706, mAb1780, mAb1773 and mAb1779 heavy and light chain variable regions were obtained (the amino acid residues of the VH/VL CDRs were determined and annotated by the Kabat numbering system):

mAb1705 murine heavy chain variable region sequence
SEQ ID NO: 6
EVQLVESGGGLVQPGRSLKLSCTASGFTFSHYYMAWVRQAPKKGLEWVT<u>SI SYEGDITYYGDSVKG</u>RFTISRDNAKSTLYLQMNSLRSEDTATYYCAS<u>QTLR ESFDY</u>WGQGVMVTVSS mAb1705 murine light chain variable region sequence
SEQ ID NO: 7
DIQMTQSPSSMSVSLGDRVTITC<u>RASQDIANYLS</u>WYQQKIARSPKLVIY<u>GT SNLEV</u>GVPSRFSGSRSGSDYSLTINTLESEDTGIYFC<u>LQDKEFPRT</u>FGGGT

RLELK mAb1706 murine heavy chain variable region sequence
SEQ ID NO: 8
EVQLVESGGGLVQPGRSLKLSCAASGFTFS<u>HYYMA</u>WVRQAPKKGLEWVT<u>SI</u>
<u>NYEGNSAYYGDSVKG</u>RFTISRDNAKSTLYLQMDSLRSEDTATYYCAT<u>ETLR</u>
<u>ESLDY</u>WGQGVMVTVSS mAb1706 murine light chain variable region sequence
SEQ ID NO: 9
DIQMTQSPSSMSVSLGDRVTTTC<u>RASQDIGNYLS</u>WYQQKLGKSPKLMIH<u>SA</u>
<u>SNLEV</u>GVPSRFSGSRSGSDYSLTINTLESEDPGIYFC<u>LQHKQFPRT</u>FGGGT
KLELK mAb1780 murine heavy chain variable region sequence
SEQ ID NO: 10
QVKLLQSGAALVKPGDSVKMSCKASDYTFT<u>EYLIH</u>WVKQSQGRSLEWIG<u>YI</u>
<u>NPYSGGTVYNEKFKS</u>KATLTVDKFSSTAYMEFRRLTFEDSAIYYCAR<u>DGGY</u>
<u>SDPLDY</u>WGQGVMVTVSS mAb1780 murine light chain variable region sequence
SEQ ID NO: 11
DTVLTQSPALAVSPGERVSISC<u>RASEGLTSYMH</u>WYQQKPGQQPKLLIY<u>KAS</u>
<u>NLAS</u>GVPARFSGSGSGTDFTLTIDPVEADDAATYFC<u>QQNWNDPWT</u>FGGGTK
LELK mAb1773 murine heavy chain variable region sequence
SEQ ID NO: 12
EVQLQQSLAELVRPGASTLSCTASGFNIK<u>NTYIH</u>WVKQRPGLEWIG<u>RIDP</u>
<u>ANGDTKHGPKFQG</u>KATITADTSSNTAYLQFSSLTSEDTAIYYCF<u>RYGIYPD</u>
<u>H</u>WGQGTPLTVSS mAb1773 murine light chain variable region sequence
SEQ ID NO: 13
QIVLTQSPALMSASPGEKVTMTC<u>SASSSVNYIY</u>WYQQKPRSSPKPWIY<u>LTA</u>
<u>TLAS</u>GVPARFSGSGSGTSFSLTISRMEAEDAATYYC<u>QQWNSYPYT</u>FGGGTK
LEIE mAb1779 murine heavy chain variable region sequence
SEQ ID NO: 14
QVKLLQSGAALVKPGDSVKMSCKASGYTFT<u>DYIIH</u>WVKQSHGKLEWIG<u>YFN</u>
<u>PNSGGSNYNENFKR</u>KATLTADKSSSTAYLEFSRVTSEDSAIYYCGR<u>RIAWD</u>
<u>HWYFDF</u>WGPGTMVTVSS mAb1779 murine light chain variable region sequence
SEQ ID NO: 15
DIQMTQSPASLSASLGETVSIEC<u>LASEGISNDVA</u>WYQQKSGRSPQLLVY<u>AA</u>
<u>SRLQD</u>GVPSRFSGSGSGTRYFFKISGMQPEDEADYFC<u>QQGYKTPLT</u>FGSGT
KLEIK The light and heavy chain CDR sequences of each antibody are shown in Table 1.

TABLE 1

Heavy and light chain CDR sequences of each antibody

| Antibody | Heavy chain | Light chain |
|---|---|---|
| mAb1705 | HCDR1 HYYMA | LCDR1 RASQDIANYLS |
|  | SEQ ID NO: 16 | SEQ ID NO: 19 |
|  | HCDR2 SISYEGDITYYGDSVKG | LCDR2 GTSNLEV |
|  | SEQ ID NO: 17 | SEQ ID NO: 20 |
|  | HCDR3 QTLRESFDY | LCDR3 LQDKEFPRT |
|  | SEQ ID NO: 18 | SEQ ID NO: 21 |
| mAb1706 | HCDR1 HYYMA | LCDR1 RASQDIGNYLS |
|  | SEQ ID NO: 22 | SEQ ID NO: 25 |
|  | HCDR2 SINYEGNSAYYGDSVKG | LCDR2 SASNLEV |
|  | SEQ ID NO: 23 | SEQ ID NO: 26 |
|  | HCDR3 ETLRESLDY | LCDR3 LQHKQFPRT |
|  | SEQ ID NO: 24 | SEQ ID NO: 27 |
| mAb1780 | HCDR1 EYLIH | LCDR1 RASEGLTSYMH |
|  | SEQ ID NO: 28 | SEQ ID NO: 31 |
|  | HCDR2 YINPYSGGTVYNEKFKS | LCDR2 KASNLAS |
|  | SEQ ID NO: 29 | SEQ ID NO: 32 |
|  | HCDR3 DGGYSDPLDY | LCDR3 QQNWNDPWT |
|  | SEQ ID NO: 30 | SEQ ID NO: 33 |
| mAb1773 | HCDR1 NTYIH | LCDR1 SASSSVNYIY |
|  | SEQ ID NO: 34 | SEQ ID NO: 37 |
|  | HCDR2 RIDPANGDTKHGPKFQG | LCDR2 LTATLAS |
|  | SEQ ID NO: 35 | SEQ ID NO: 38 |
|  | HCDR3 YGIYPDH | LCDR3 QQWNSYPYT |
|  | SEQ ID NO: 36 | SEQ ID NO: 39 |
| mAb1779 | HCDR1 DYIIH | LCDR1 LASEGISNDVA |
|  | SEQ ID NO: 40 | SEQ ID NO: 43 |
|  | HCDR2 YFNPNSGGSNYNENFKR | LCDR2 AASRLQD |
|  | SEQ ID NO: 41 | SEQ ID NO: 44 |
|  | HCDR3 RIAWDHWYFDF | LCDR3 QQGYKTPLT |
|  | SEQ ID NO: 42 | SEQ ID NO: 45 |

The activity results of Biacore assay are shown in Table 2.

TABLE 2

In vitro activity of IL-5 murine antibody

| antibody | affinity to HuIL-5 (KD (M)) |
|---|---|
| mAb1705 | 7.27E-11 |
| mAb1706 | 3.83E-11 |
| mAb1780 | 8.99E-11 |
| mAb1773 | 1.29E-10 |
| mAb1779 | 4.58E-10 |

The results show that the murine antibodies of the present disclosure have high affinity to the antigen.

Example 4: Purification of IL-5-Related Recombinant Proteins, and Purification of Hybridoma Antibodies and Recombinant Antibodies 4.1 Steps for Purification of IL-5-Flag-His Recombinant Proteins:

Samples were centrifuged at high speed to remove impurities and concentrated to appropriate volume. The NI-NTA affinity column (QIAGEN, Cat No. 30721) was equilibrated with PBS and washed with 2-5 column volumes. The cell-expressed supernatants without impurities were loaded onto the column, which was then rinsed with PBS until the A280 reading was dropped to the baseline. Then the column was rinsed with PBS to remove the impure protein. The protein of interest was eluted with washing buffer (imidazole 20 mM) and then elution buffer (imidazole 300 mM), and the eluted peak was collected.

The collected elute was further purified by ion exchange (Hiload 16/600 superdex 200 column). The column was equilibrated with about 2 column volumes of PBS to ensure pH of 7.4. The elution buffer containing the protein of interest was concentrated and loaded onto the column for subsequent purification, the samples were collected, identified by SDS-PAGE and LC-MS, and then aliquoted for use.

4.2. Purification of Hybridoma-Expressed Antibody and Fc Fusion Proteins

The cell-expressed supernatant samples were centrifuged at high speed to remove impurities, and then the hybridoma-expressed supernatants were purified by using Protein G column, the Fc fusion protein expressing supernatants were purified by using Protein A column. The column was rinsed with PBS until the A280 reading was dropped to the baseline. The proteins of interest were eluted with 100 mM acetic acid, pH 3.0 and neutralized with 1 M Tris-HCl, pH 8.0. The eluted samples were appropriately concentrated and further purified by gel chromatography Superdex 200 (GE) pre-equilibrated with PBS. The peaks deprived of aggregates were collected and aliquoted for use.

Example 5: Humanization Design of Anti-Human IL-5 Monoclonal Antibodies

Humanization of murine anti-human IL-5 monoclonal antibodies was carried out as disclosed in literatures in the art. Briefly, the constant regions of murine antibodies were replaced with human constant regions, the CDRs of murine antibodies were grafted onto the human template sharing the highest FR homology, and some amino acid residues in FR region, which have key effect on maintaining the antibody conformation and affecting the binding of the antibody to the antigen, were back-mutated.

By aligning to IMGT human antibody heavy and light chain variable region germline gene database, human germline heavy and light chain variable region genes, which have high identity to amino acid sequence of mAb-1705, mAb-1706, mAb1780, mAb1773 and mAb1779 antibody, were selected as templates respectively. The CDRs of these murine antibodies were separately grafted onto the corresponding human derived templates to form a variable region sequence in the order of FR1-CDR1-FR2-CDR2-FR3-CDR3-FR4. The amino acid residues were determined and annotated by the Kabat numbering system.

Selection of Human FR Region and Back Mutation of Key Amino Acids

Based on the typical VH/VL CDR structure of the obtained murine antibody, homologous sequences of light chain variable region (VL) and heavy chain variable region (VH) was selected from the human germline database. The resulting human germline VL and VH sequences were ranked from high to low, based on FR homology, and the germline sequences with the highest FR homology were selected as main templates. The CDRs of the murine antibodies were grafted onto the human templates. And then by using software and based on the three-dimensional structure of the murine antibodies, the embedded residues, residues which interact directly with the CDR regions, and residues which have significant effects on the conformation of VL and VH were subjected to back mutations. Further, chemically unstable amino acid residues were optimized to yield final humanized molecules.

5.1 Selection of Humanized Framework for Hybridoma Clone mAb1705

IGHV3-23*04 was selected as the template for h1705 VH, and IGKV1-12*01 was selected as the template for VL. The CDRs of murine mAb1705 were grafted onto the human template. The embedded residues and residues which interact directly with the CDR regions were found by software and were subjected to back-mutation. The light and heavy chain variable regions of the humanized antibodies were designed as shown in Table 3.

TABLE 3

Selection of template and design of back mutation for h1705

| h1705_VL | | h1705_VH | |
|---|---|---|---|
| h1705_VL.1 | Grafted | h1705_VH.1 | Grafted |
| h1705_VL.1A | A43S, G66R | h1705_VH.1A | K98S |
| h1705_VL.1B | A43S, L47V, G66R, T69S, F71Y Y87F | h1705_VH.1B | S49T, V93T, K98S |

Note:
"Grafted" means the murine antibody CDRs were grafted onto the human germline FR region sequence. For example, A43S indicates that A on position 43 of the grafted sequence was back-mutated to S, according to the natural sequence numbering of the amino acid sequence.

TABLE 4

Combination of h1705 humanized antibody heavy and light chain variable region

| | h1705_VH.1 | h1705_VH.1A | h1705_VH.1B |
|---|---|---|---|
| h1705_VL.1 | h1705-003 | h1705-004 | h1705-005 |
| h1705_VL.1A | h1705-006 | h1705-007 | h1705-008 |
| h1705_VL.1B | h1705-009 | h1705-010 | h1705-011 |

Note:
This table shows sequences obtained by combining various variants. For example, H1705-007 indicates that the humanized murine antibody h1705-007 comprises two variants, i.e., light chain h1705_VL.1A and heavy chain h1705_VH.1A, and so forth.

The specific sequence of variable regions of humanized antibody h1705 are as follows:

h1705_VL.1
(SEQ ID NO: 46)
DIQMTQSPSSVSASVGDRVTTTCRASQDIANYLSWYQQKPGKAPKLLIYGT

SNLEVGVPSRFSGSGSGTDFTLTISSLQPEDFATYYCLQDKEFPRTFGGGT

KVEIK h1705_VL.1A
(SEQ ID NO: 47)
DIQMTQSPSSVSASVGDRVTITCRASQDIANYLSWYQQKPGKSPKLLIYGT

SNLEVGVPSRFSGSRSGTDFTLTISSLQPEDFATYYCLQDKEFPRTFGGGT

KVEIK h1705_VL.1B
(SEQ ID NO: 48)
DIQMTQSPSSVSASVGDRVTITCRASQDIANYLSWYQQKPGKSPKLVIYGT

SNLEVGVPSRFSGSRSGSDYTLTISSLQPEDFATYFCLQDKEFPRTFGGGT

KVEIK h1705_VH.1
(SEQ ID NO: 49)
EVQLVESGGGLVQPGGSLRLSCAASGFTFSHYYMAWVRQAPGKGLEWVSSI

SYEGDITYYGDSVKDRFTISRDNSKNTLYLQMNSLRAEDTAVYYCAKQTLR

ESFDYWGQGTLVTVSS h1705_VH.1A (SEQ ID NO: 50)
EVQLVESGGGLVQPGGSLRLSCAASGFTFSHYYMAWVRQAPGKGLEWVSSI

SYEGDITYYGDSVKGRFTISRDNSKNTLYLQMNSLRAEDTAVYYCASQTLR

ESFDYWGQGTLVTVSS h1705_VH.1B (SEQ ID NO: 51)
EVQLVESGGGLVQPGGSLRLSCAASGFTFSHYYMAWVRQAPGKGLEWVTSI

SYEGDITYYGDSVKGRFTISRDNSKNTLYLQMNSLRAEDTATYYCASQTLR

ESFDYWGQGTLVTVSS

Each of the above light chain variable regions was combined with light chain constant region as set forth in SEQ ID NO: 53 to form the final intact light chain sequences. Each heavy chain variable region was combined with heavy chain constant region as set forth in SEQ ID NO: 52 to form the final heavy chain sequences.

Humanized Antibody Constant Region Sequence

```
Heavy chain IgG1 constant region:
                              SEQ ID NO: 52
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPELLGGPSVFLFPPKPKDTLYITREPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSLSPGK
Note:
Underlined text represents the designed M252Y,
S254T or T256E mutation.

Light chain kappa constant region:
                              SEQ ID NO: 53
RTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSF

NRGEC
```

5.2 Selection of Humanized Framework for Hybridoma Clone mAb1706

IGHV3-23*04 was selected as the template for h1706 VH, and IGKV1-12*01 was selected as the template for VL. The CDRs of murine mab1706 were grafted onto the human template. The embedded residues and residues which interact directly with the CDR regions were found by software and were subjected to back-mutation. The light and heavy chain variable regions of the humanized antibodies were designed as shown in Table 5.

TABLE 5

Selection of template and design of back mutation for h1706

| h1706_VL | | h1706_VH | |
|---|---|---|---|
| h1706_VL.1 | Grafted | h1706_VH.1 | Grafted |
| h1706_VL.1A | A43S | h1706_VH.1A | K98T |
| h1706_VL.1B | A43S, L47M, F71Y, Y87F | h1706_VH.1B | S49T, V93T, K98T |

Note:
"Grafted" means the murine antibody CDRs were grafted onto the human germline FR region. For example, A43S indicates that A on position 43 of the grafted sequence was back-mutated to S, according to the natural sequence numbering of the amino acid sequence.

TABLE 6

Combination of h1706 humanized antibody heavy and light chain variable region

| | h1706_VH.1 | h1706_VH.1A | h1706_VH.1B |
|---|---|---|---|
| h1706_VL.1 | h1706-002 | h1706-003 | h1706-004 |
| h1706_VL.1A | h1706-005 | h1706-006 | hl706-007 |
| h1706_VL.1B | h1706-008 | h1706-009 | hl706-010 |

The specific sequences of the variable regions of humanized antibody h1706 are shown as follows:

h1706_VL.1

(SEQ ID NO: 54)
DIQMTQSPSSVSASVGDRVTITCRASQDIGNYLSWYQQKPGKAPKLLIYSA

SNLEVGVPSRFSGSGSGTDFTLTISSLQPEDFATYYCLQHKQFPRTFGGGT

KVEIK h1706_VL.1A (SEQ ID NO: 55)
DIQMTQSPSSVSASVGDRVTITCRASQDIGNYLSWYQQKPGKSPKLLIYSA

SNLEVGVPSRFSGSGSGTDFTLTISSLQPEDFATYYCLQHKQFPRTFGGGT

KVEIK h1706_VL.1B (SEQ ID NO: 56)
DIQMTQSPSSVSASVGDRVTITCRASQDIGNYLSWYQQKPGKSPKLMIYSA

SNLEVGVPSRFSGSGSGTDYTLTISSLQPEDFATYFCLQHKQFPRTFGGGT

KVEIK h1706_VH.1

(SEQ ID NO: 57)
EVQLVESGGGLVQPGGSLRLSCAASGFTFSHYYMAWVRQAPGKGLEWVSSI

NYEGNSAYYGDSVKGRFTISRDNSKNTLYLQMNSLRAEDTAVYYCAKETLR

ESLDYWGQGTMVTVSS h1706_VH.1A (SEQ ID NO: 58)
EVQLVESGGGLVQPGGSLRLSCAASGFTFSHYYMAWVRQAPGKGLEWVSSI

NYEGNSAYYGDSVKGRFTISRDNSKNTLYLQMNSLRAEDTAVYYCATETLR

ESLDYWGQGTMVTVSS h1706_VH.1B (SEQ ID NO: 59)
EVQLVESGGGLVQPGGSLRLSCAASGFTFSHYYMAWVRQAPGKGLEWVTSI

NYEGNSAYYGDSVKGRFTISRDNSKNTLYLQMNSLRAEDTATYYCATETLR

ESDLYWGQGTMVTVSS

Each of the above light chain variable regions was combined with light chain constant region as set forth in SEQ ID NO: 53 to form the final intact light chain sequences. Each heavy chain variable region was combined with heavy chain constant region as set forth in SEQ ID NO: 52 to form the final heavy chain sequences.

5.3 Selection of Humanized Framework for Hybridoma Clone mAb1780

IGHV1-2*02 was selected as the template for h1780 VH, and IGKV3-11*01 was selected as the template for VL. The CDRs of murine mAb1780 were grafted onto the human template. The embedded residues and residues which interact directly with the CDR regions were found by software and were subjected to back-mutation. The light and heavy chain variable regions of the humanized antibodies were designed as shown in Table 7.

TABLE 7

Selection of template and design of back mutation for h1780

| h1780_VL | | h1780_VH | |
|---|---|---|---|
| h1780_VL.1 | Grafted | h1780_VH.1 | Grafted |
| h1780_VL.1A | E1D, I2T | h1780_VH.1A | M70L, R72V, T74K |
| h1780_VL.1B | E1D, I2T, I57V, V84T, Y86F | h1780_VH.1B | M48L V68A, M70L, R72V, T74K, L83F |
| | | h1780_VH.1C | R38K, M48I, R67K, V68A, M70L, R72V, T74K, L83F |

Note:
"Grafted" means the murine antibody CDRs were grafted onto the human germline FR region. For example, E1D indicates that E on position 1 of the grafted sequence was back-mutated to D, according to the natural sequence numbering of the amino acid sequence.

TABLE 8

Combination of h1780 humanized antibody heavy and light chain variable region

| | h1780_VH.1 | h1780_VH.1A | h1780_VH.1B | h1780_VH.1C |
|---|---|---|---|---|
| h1780_VL.1 | h1780-007 | h1780-008 | h1780-009 | h1780-010 |
| h1780_VL.1A | h1780-011 | h1780-012 | h1780-013 | h1780-014 |
| h1780_VL.1B | h1780-015 | h1780-016 | h1780-017 | h1780-018 |

The specific sequences of the variable regions of humanized antibody h1780 are shown as follows:

h1780_VL.1
(SEQ ID NO: 60)
EIVLTQSPATLSLSPGERATLSCRASEGLTSYMHWYQQKPGQAPRLLIYKA

SNLASGIPARFSGSGSGTDFTLTISSLEPEDFAVYYCQQNWNDPWTFGGGT

KVEIK h1780_VL.1A
(SEQ ID NO: 61)
DTVLTQSPATLSLSPGERATLSCRASEGLTSYMHWYQQKPGQAPRLLIYKA

SNLASGIPARFSGSGSGTDFTLTISSLEPEDFAVYYCQQNWNDPWTFGGGT

KVEIK h1780_VL.1B
(SEQ ID NO: 62)
DTVLTQSPATLSLSPGERATLSCRASEGLTSYMHWYQQKPGQAPRLLIYKA

SNLASGVPARFSGSGSGTDFTLTISSLEPEDFATYFCQQNWNDPWTFGGGT

KVEIK h1780_VH.1
(SEQ ID NO: 63)
EVQLVQSGAEVKKPGASVKVSCKASGYTFTEYLIHWVRQAPGQGLEWMGYI

NPYSGGTVYNEKFKSRVTMTRDTSISTAYMELSRLRSDDTAVYYCARDGGY

SDPLDYWGQGTMVTVSS h1780_VH.1A
(SEQ ID NO: 64)
EVQLVQSGAEVKKPGASVKVSCKASGYTFTEYLIHWVRQAPGQGLEWMGYI

NPYSGGTVYNEKFKSRVTLTVDKSISTAYMELSRLRSDDTAVYYCARDGGY

SDPLDYWGQGTMVTVSS

-continued h1780_VH.1B
(SEQ ID NO: 65)
EVQLVQSGAEVKKPGASVKVSCKASGYTFTEYLIHWVRQAPGQGLEWIGYI

NPYSGGTVYNEKFKSRATLTVDKSISTAYMEFSRLRSDDTAVYYCARDGGY

SDPLDYWGQGTMVTVSS h1780_VH.1C
(SEQ ID NO: 66)
EVQLVQSGAEVKKPGASVKVSCKASGYTFTEYLIHWVKQAPGQGLEWIGYI

NPYSGGTVYNEKFKSKATLTVDKSISTAYMEFSRLRSDDTAVYYCARDGGY

SDPLDYWGQGTMVTVSS

Each of the above light chain variable regions was combined with light chain constant region as set forth in SEQ ID NO: 53 to form the final intact light chain sequences. Each heavy chain variable region was combined with heavy chain constant region as set forth in SEQ ID NO: 52 to form the final heavy chain sequences.

5.4 Selection of Humanized Framework for Hybridoma Clone mAb1773

IGHV3-73*01 was selected as the template for h1773 VH, and IGKV1-39*01 was selected as the template for VL. The CDRs of murine mAb1773 were grafted onto the human template. The embedded residues and residues which interact directly with the CDR regions were found by software and were subjected to back-mutation. The light and heavy chain variable regions of the humanized antibodies were designed as shown in Table 9. Meanwhile, in order to eliminate isomerized sites in CDR regions, N located in HCDR2 (RIDPANGDTK HGPKFQG) of h1773 was replaced with V (i.e., N55V) to form a heavy chain variable region and an antibody comprising HCDR2 variant (the sequence of the mutated HCDR2 is shown as SEQ ID NO: 82: RIDPAVGDTKHGPKFQG).

TABLE 9

Selection of template and design of back mutation for h1773

| h1773_VL | | h1773_VH | |
|---|---|---|---|
| h1773_VL.1 | Grafted | h1773_VH.1 | Grafted |
| h1773_VL.1A | M4L, A42S, L45P, L46W | h1773_VH.1A | F29I, R72A, T97F + N55V |
| | | h1773_VH.1B | F29I, R38K, V48I, R72A, T97F + N55V |

Note:
"Grafted" means the murine antibody CDRs were grafted onto the human germline FR region. For example, M4L indicates that M on position 4 of the grafted sequence was back-mutated to L, according to the natural sequence numbering of the ammo acid sequence.

TABLE 10

Combination of h1773 humanized antibody heavy and light chain variable region

| | h1773_VH.1 | h1773_VH.1A | h1773_VH.1B |
|---|---|---|---|
| h1773_VL.1 | h1773-002 | h1773-003 | h1773-004 |
| h1773_VL.1A | h1773-005 | h1773-006 | h1773-007 |

The specific sequences of the variable regions of humanized antibody h1773 are shown as follows:

h1773_VL.1
(SEQ ID NO: 67)
DIQMTQSPSSLSASVGDRVTITCSASSSVNYIYWYQQKPGKAPKLLIYLTA

TLASGVPSRFSGSGSGTDFTLTISSLQPEDFATYYCQQWNSYPYTFGGGTK

VEIK h1773_VL.1A
(SEQ ID NO: 68)
DIQLTQSPSSLSASVGDRVTITCSASSSVNYIYWYQQKPGKSPKPWIYLTA

TLASGVPSRFSGSGSGTDFTLTISSLQPEDFATYYCQQWNSYPYTFGGGTK

VEIK h1773_VH.1
(SEQ ID NO: 69)
EVQLVESGGGLVQPGGSLKLSCAASGFTFSNTYIHWVRQASGKGLEWVGRI

DPAVGDTKHGPKFQGRFTISRDDSKNTAYLQMNSLKTEDTAVYYCTRYGIY

PDHWGQGTLVTVSS h1773_VH.1A
(SEQ ID NO: 70)
EVQLVESGGGLVQPGGSLKLSCAASGFTISNTYIHWVRQASGKGLEWVGRI

DPAVGDTKHGPKFQGRFTISADDSKNTAYLQMNSLKTEDTAVYYCFRYGIY

PDHWGQGTLVTVSS h1773_VH.1B
(SEQ ID NO: 71)
EVQLVESGGGLVQPGGSLKLSCAASGFTISNTYIHWVKQASGKGLEWIGRI

DPAVGDTKHGPKFQGRFTISADDSKNTAYLQMNSLKTEDTAVYYCFRYGIY

PDHWGQGTLVTVSS

Each of the above light chain variable regions was combined with light chain constant region as set forth in SEQ ID NO: 53 to form the final intact light chain sequences. Each heavy chain variable region was combined with heavy chain constant region as set forth in SEQ ID NO: 52 to form the final heavy chain sequences.

5.5 Selection of Humanized Framework for Hybridoma Clone mAb1779

IGHV1-2*02 was selected as the template for h1779 VH, and IGKV1-33*01 was selected as the template for VL. The CDRs of murine h1779 were grafted onto the human template. The embedded residues and residues which interact directly with the CDR regions were found by software and were subjected to back-mutation. The light and heavy chain variable regions of the humanized antibodies were designed as shown in Table 11.

TABLE 11

Selection of template and design of back mutation for h1779

| h1779_VL | | h1779_VH | |
|---|---|---|---|
| h1779_VL.1 | Grafted | h1779_VH.1 | Grafted + D89E |
| h1779_VL.1A | A43S | h1779_VH.1A | R72A, T74K + D89E |
| h1779_VL.1B | A43S, I48V, F71Y | h1779_VH.1B | M48I, V68A, R72A, T74K + D89E |
| | | h1779_VH.1C | M48I, VA5A, R72A, T74K, M81L, L83F + D89E |

TABLE 11-continued

Selection of template and design of back mutation for h1779

| h1779_VL | h1779_VH |
|---|---|
| | h1779_VH.1D    R38K, M48L R67K, V68A, R72A, T74K, M81L, L83F + D89E |

Note:
"Grafted" means the murine antibody CDRs were grafted onto the human germline FR region. For example, A43S indicates that A on position 43 of the grafted sequence was back-mutated to S, according to the natural sequence numbering of the amino acid sequence.

The designed humanized molecules were combined to various molecules as indicated in Table 12.

TABLE 12

Combination of h1779 humanized antibody heavy and light chain variable region

| | h1779_VH.1 | h1779_VH.1A | h1779_VH.1B | h1779_VH.1C | h1779_VH.1D |
|---|---|---|---|---|---|
| h1779_VL.1 | h1779-005 | h1779-006 | h1779-007 | h1779-008 | h1779-009 |
| h1779_VL.1A | h1779-010 | h1779-011 | h1779-012 | h1779-013 | h1779-014 |
| h1779_VL.1B | h1779-015 | h1779-016 | h1779-017 | h1779-018 | h1779-019 |

The specific sequences of the variable regions of humanized antibody h1779 are shown as follows:

h1779_VL.1
(SEQ ID NO: 72)
DIQMTQSPSSLSASVGDRTITCLASEGISNDVAWYQQKPGKAPKLLIYAAS

RLQDGVPSRFSGSGSGTDFTFTISSLQPEDIATYYCQQGYKTPLTFGQGTK

LEIK h1779_VL.1A
(SEQ ID NO: 73)
DIQMTQSPSSLSASVGDRVTITCLASEGISNDVAWYQQKPGKSPKLLIYAA

SRLQDGVPSRFSGSGSGTDFTFTISSLQPEDIATYYCQQGYKTPLTFGQGT

KLEIK h1779_VL.1B
(SEQ ID NO: 74)
DIQMTQSPSSLSASVGDRVTITCLASEGISNDVAWYQQKPGKSPKLLVYAA

SRLQDGVPSRFSGSGSGTDYTFTISSLQPEDIATYYCQQGYKTPLTFGQGT

KLEIK h1779_VH.1
(SEQ ID NO: 75)
EVQLVQSGAEVKKPGASVKVSCKASGYTFTDYIIHWVRQAPGQGLEWMGYF

NPNSGGSNYNENFKRRVTMTRDTSISTAYMELSRLRSEDTAVYYCARRIAW

DHWYFDFWGQGTMVTVSS h1779_VH.1A
(SEQ ID NO: 76)
EVQLVQSGAEVKKPGASVKVSCKASGYTFTDYIIHWVRQAPGQGLEWMGYF

NPNSGGSNYNENFKRRVTMTADKSISTAYMELSRLRSEDTAVYYCARRIAW

DHWYFDFWGQGTMVTVSS h1779_VH.1B
(SEQ ID NO: 77)
EVQLVQSGAEVKKPGASVKVSCKASGYTFTDYIIHWVRQAPGQGLEWIGYF

NPNSGGSNYNENFKRRATMTADKSISTAYMELSRLRSEDTAVYYCARRIAW

DHWYFDFWGQGTMVTVSS h1779_VH.1C
(SEQ ID NO: 78)
EVQLVQSGAEVKKPGASVKVSCKASGYTFTDYIIHWVRQAPGQGLEWIGYF

NPNSGGSNYNENFKRRATMTADKSISTAYLEFSRLRSEDTAVYYCARRIAW

DHWYFDFWGQGTMVTVSS h1779_VH.1D
(SEQ ID NO: 79)
EVQLVQSGAEVKKPGASVKVSCKASGYTFTDYIIHWVKQAPGQGLEWIGYF

NPNSGGSNYNENFKRKATMTADKSISTAYLEFSRLRSEDTAVYYCARRIAW

DHWYFDFWGQGTMVTVSS

Each of the above light chain variable regions was combined with light chain constant region as set forth in SEQ ID NO: 53 to form the final intact light chain sequences. Each heavy chain variable region was combined with heavy chain constant region as set forth in SEQ ID NO: 52 to form the final heavy chain sequences.

Meanwhile, antibody Hu39D10 against IL5 disclosed in WO2012083370A1 was used as a positive control in the present disclosure, and the heavy and light chain sequence thereof is shown in SEQ ID NO: 80 and SEQ ID NO: 81, respectively.

Heavy chain sequence of Hu39D10
SEQ ID NO: 80
EVQLVESGGGLVQPGGSLRLSCAVSGLSLTSNSVNWIRQAPGKGLEWVGLI

WSNGDTDYNSAIKSRFTISRDTSKSTVYLQMNSLRAEDTAVYYCAREYYGY

FDYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDHK

PSNTKVDKRVESKYGPPCPPCPAPEFLGGPSVFLFPPKPKDTLMISRTPEV

TCVVVDVSQEDPEVQFNWYVDGVEVHNAKTKPREEQFNSTYRVVSVLTVLH

QDWLNGKEYKCKVSNKGLPSSIEKTISKAKGQPREPQVYTLPPSQEEMTKN

-continued

QVSLTCLVKGFYPSDIAVEWESNGQPENNYKTTPPVLDSDGSFFLYSRLTV

DKSRWQEGNVFSCSVMHEALHNHYTQKSLSLSLGK

Light chain sequence of Hu39D10
SEQ ID NO: 81
DIQMTQSPSSLSASVGDRVTITCLASEGISSYLAWYQQKPGKAPKLLIYGA

NSLQTGVPSRFSGSGSATDYTLTISSLQPEDFATYYCQQSYKFPNTFGQGT

KVEVKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

Example 6. Preparation of Recombinant Chimeric Antibodies and Humanized Antibodies 1. Molecular Cloning of Recombinant Chimeric Antibodies The positive antibody molecules obtained by hybridoma screening were sequenced to obtain gene sequences encoding the variable regions. Forward and reverse primers were designed on the basis of the obtained sequences, and VH/VK gene fragment of each antibody was constructed via PCR by using the gene sequence as a template. The VH/VK gene fragment was then subjected to homologous recombination with expression vector pHr (comprising a signal peptide and hIgG1/hkappa constant region gene (CH1-Fc/CL) fragment) to construct a recombinant chimeric antibody full-length expression plasmid VH-CH1-Fc-pHr/VL-CL-pHr to form five chimeric antibodies of Ch1705, Ch1706, Ch1780, Ch1773 and Ch1779.

2. Molecular Cloning of Humanized Antibodies

Codon-optimization was performed on the designed humanized antibody sequences to generate coding gene sequences with human codon-preference. PCR primers were designed to construct the VH/VK gene fragment of each antibody, and then the VH/VK gene fragment was subjected to homologous recombination with expression vector pHr (comprising a signal peptide and hIgG1/hkappa constant region gene (CH1-Fc/CL) fragment) to construct humanized antibody full-length expression plasmid VH-CH1-Fc-pHr-VL-CL-pHr.

3. Expression and Purification of Recombinant Chimeric Antibodies and Humanized Antibodies The plasmid expressing the antibody light or heavy chain was transfected into HEK293E cells at a ratio of 1:1.2. After 6 days, the expression supernatants were collected, centrifuged at high speed to remove impurities, and purified by protein A column. The column was rinsed with PBS until the A280 reading was dropped to the baseline. The protein of interest was eluted with acidic elution buffer, pH 3.0-pH 3.5 and neutralized with 1 M Tris-HCl, pH 8.0-9.0. The eluted samples were appropriately concentrated, and further purified by gel chromatography Superdex 200 (GE) pre-equilibrated with PBS to remove the aggregates. The monomer peak was collected and aliquoted for use.

The performance and beneficial effects of the antibodies in present disclosure were verified by the following test methods.

In Vitro Evaluation of Biological Activity

Test Example 1: Binding of Murine IL-5 Antibodies to IL-5 of Different Species by Biacore Assay The affinity between the test murine IL-5 antibodies and human IL-5 was determined by using Biacore T200 (GE) instrument.

Molecules to be tested were affinity-captured by Protein A biosensor chip, and then the antigen (the recombinant human, monkey and murine IL5 prepared in Example 1) was flowed through the surface of the chip, and the reaction signals were detected in real time by using Biacore T200 instrument to obtain binding and dissociation curves. After the dissociation of each cycle of experiment was completed, the biosensor chip was washed and regenerated with glycine-hydrochloric acid regeneration solution (pH 1.5). The data was fitted to the (1:1) Langmuir model by using BIAevaluation version 4.1 GE software, and the affinity values were obtained as shown in Table 13.

TABLE 13

Results of affinity of murine IL-5 antibodies to IL-5 of different species by BIAcore assay

| antigen | KD (M) | | | | |
|---|---|---|---|---|---|
| | mAb1705 | mAb1706 | mAb1780 | mAb1773 | mAb1779 |
| Human IL-5 | 7.27E−11 | 3.83E−11 | 8.99E−11 | 1.29E−10 | 4.58E−10 |
| Monkey IL-5 | 2.05E−10 | 2.77E−10 | 3.12E−10 | 4.76E−10 | 9.98E−9 |

This example demonstrates that all of the antibodies mAb 1705, mAb 1706, mAb 1780, mAb 1773 and mAb 1779 of the present disclosure have high affinity to IL-5 of different species (human, monkey).

Test Example 2: Affinity of Humanized IL-5 Antibodies to IL-5 of Different Species by Biacore Assay The affinity between the test humanized IL-5 antibodies and human IL-5 was determined by using Biacore T200 (GE) instrument.

Molecules to be tested were affinity-captured by Protein A biosensor chip, and then the antigen (prepared in Example 1) was flowed through the surface of the chip, and the reaction signals were detected in real time by using Biacore T200 instrument to obtain binding and dissociation curves. After the dissociation of each cycle of experiment was completed, the biosensor chip was washed and regenerated with glycine-hydrochloric acid regeneration solution (pH 1.5). The data was fitted to the (1:1) Langmuir model by using BIAevaluation version 4.1 GE software, and the affinity values were obtained as shown in Table 14.

TABLE 14

Results of affinity of humanized IL-5 antibodies to human IL-5 by BIAcore assay

| antibody | KD(M) | antibody | KD(M) |
|---|---|---|---|
| h1705-003 | 3.35E−09 | h1706-003 | 1.89E−11 |
| h1705-006 | 4.11E−09 | h1706-006 | 1.73E−11 |

TABLE 14-continued

Results of affinity of humanized IL-5 antibodies
to human IL-5 by BIAcore assay

| antibody | KD(M) | antibody | KD(M) |
|---|---|---|---|
| h1705-009 | 4.55E−09 | h1706-009 | 5.45E−11 |
| h1705-004 | 2.14E−11 | h1780-017 | 7.78E−11 |
| h1705-007 | 2.21E−11 | h1773-007 | 2.07E−10 |
| h1705-010 | 2.05E−11 | h1779-014 | 4.12E−10 |
| h1705-005 | 2.16E−11 | | |
| h1705-008 | 3.42E−11 | | |
| h1705-011 | 2.30E−11 | | |

The results show that the humanized IL-5 antibodies still have high affinity to human IL-5 (as for humanized variants of the other murine antibodies, only exemplary data were provided, except for each humanized variant of h1705).

Test Example 3: Murine IL-5 Antibodies Block the Binding Between IL-5 and IL-5α Receptor by ELISA Assay To demonstrate the ability of IL-5 antibodies to prevent IL-5 from binding to the extracellular region of recombinantly expressed IL-5α receptor protein, ELISA plate was coated with IL-5 (5 μg/ml in PBS), incubated at 37° C. for 1 hour, the liquid was discarded, then 5% skim milk blocking solution diluted with PBS was added at 200 μl/well, and blocked at 37° C. for 2.5 hours in an incubator. After the blocking was finished, the blocking solution was discarded, the plate was washed 5 times with PBST buffer (PBS containing 0.05% Tween-20, pH 7.4), 25 μl of 10 μg/ml IL-5Rα (in 1% BSA) which was labeled with the biotin labeling kit (Dojindo Chemical, LK03) was added, and then 25 μl of gradient-diluted antibody which competed with IL-5Rα for binding to IL-5 was added, and incubated at 37° C. for 1 hour. After the incubation, the reaction solution in the plate was discarded, the plate was washed 5 times with PBST, Streptavidin-Peroxidase Polymer (Sigma, S2438-250UG) diluted at 1:600 with sample diluting solution was added at 50 μl/well, and incubated at 37° C. for 1 hour. After washing the plate with PBST for 5 times, 50 μl/well TMB chromogenic substrate (KPL, 52-00-03) was added, incubated at room temperature for 3-10 min, and 50 μl/well 1 M $H_2SO_4$ was added to stop the reaction. Absorbance values were read at 450 nm with NOVOStar microplate reader. The IC50 values for IL-5 antibodies to block the binding between IL-5 and IL-5Rα were calculated. The results are shown in Table 15, both antibodies of the present disclosure can effectively inhibit the binding of IL-5 to its receptor.

TABLE 15

Results of murine IL-5 antibodies to block the
binding between IL-5 and IL-5α receptor by ELISA

| | mAb1705 | mAb1706 |
|---|---|---|
| IC50 (μg/ml) | 0.42 | 0.40 |

Test Example 4: IL-5 Antibodies Block the Binding Between IL-5 and IL-5 Receptor by FACS To identify the resulting IL-5 antibodies which can block the IL-5 receptor on cell surface, we constructed recombinant cell line CHOS, which highly expresses both receptors of IL-5Rα/β. This experiment identified that IL-5 antibodies can prevent IL-5 from binding to the recombinant IL-5α/β receptor on the surface of CHOS cell line, respectively.

Particular method: CHO-S-IL-5Rα and β were cultivated with CD-CHO containing 100 ng/ml G418 and 25 ng/ml zeozin, and the concentration during cell culture was no more than $3 \times 10^6$ cells/ml. The IL-5Rα/β-CHOS cells in good condition were centrifuged (1000 rpm, 5 min), washed once with 10% FBS in PBS, counted, the cell concentration was adjusted to $4 \times 10^6$ cells/ml, and 25 μl of which was added to 96-well plate with round bottom. Antibodies to be tested were diluted with PBS solution containing 10% FBS, with an initial concentration of 200 μg/ml, and 8 gradients were obtained by 1:10 dilution. 25 μl of 100 ng/ml IL-5 labeled with Biotin Labeling Kit (Dojindo Chemical, LK03), was uniformly mixed with 50 μl of each diluted antibody, added into the 96-well plate to which the cells has been added, and incubated at 4° C. for 1 hour. After the incubation, centrifuged at 4° C. (400 g, 5 min), the supernatant was discarded, centrifuged and washed with 200 μl of pre-cooled PBS, repeat twice; PE-Avidin secondary antibody diluted at 1:1333 was added and incubated in darkness at 40° C. for 40 min, the supernatant was discarded after being centrifuged at 4° C. (400 g, 5 min), 200 μl of pre-cooled PBS was added, the cells were dissociated, centrifuged and washed at 4° C., repeated three times, and 100 μl PBS was added. The plate was read on instrument, and IC50 values for IL-5 antibodies to block the binding between IL-5 and IL-5Rα/β were calculated based on the fluorescence signal values. The results are shown in Table 16 and FIG. 1.

TABLE 16

Results of IL-5 antibodies to block the binding between IL-5 and IL-5Rα/β

| | IgG | hu39D10 | h1705-008 | h1706-009 | h1780-017 | h1773-007 | h1779-014 |
|---|---|---|---|---|---|---|---|
| IC50 (ng/ml) | 8777 | 25.07 | 14.51 | 24.74 | 16 | — | 49.64 |

The results show that the antibodies h1705-008, h1706-009, h1780-017, h1773-007 and h1779-014 showed stronger ability to block the binding of IL-5 to IL-5 receptor on cell surface.

Test Example 5: IL-5 Antibodies Inhibit IL-5-Induced Proliferation of TF1 Cells

IL-5 can induce proliferation of TF-1 cells, and IL-5 antibodies can prevent IL-5 from stimulating proliferation of TF-1 cells.

Specifically, TF-1 cells (ATCC, CRL-2003) were cultivated in RPMI1640 containing 10% FBS and 2 ng/mL rhGM-CSF (Lianke Bio, Catalog No. 96-AF-300-03-20), incubated in an incubator at 37° C., 5% $CO_2$, with the cell density of no more than $1\times10^6$ cells/ml. For detection of the antibodies, the cells being in logarithmic growth phase were washed three times with PBS by centrifuging at 800 rpm for 5 min, and the cell density was adjusted to 6000 cells/well/ 90 μl with RPMI1640 (FBS: 2%, recombinant human IL-5: 10 ng/ml). 10 μl of gradient dilutions of antibodies to be tested were added into 96-well plate and cultivated for 3 days. 30 μl of cell titer was added and mixed. The IC50 values were calculated based on the reading. The results are shown in Table 17 below.

TABLE 17

Results of IL-5 humanized antibodies to inhibit IL-5-induced proliferation of TF1 cells

| antibody | IC50 (nM) | antibody | IC50 (nM) |
| --- | --- | --- | --- |
| Hu39D10 | 0.30 | h1706-003 | 0.31 |
| h1705-004 | 0.30 | h1706-004 | 0.30 |
| h1705-005 | 0.30 | h1706-006 | 0.34 |
| h1705-007 | 0.25 | h1706-007 | 0.28 |
| h1705-008 | 0.20 | h1706-009 | 0.25 |
| h1705-010 | 0.30 | h1773-007 | 0.38 |
| h1705-011 | 0.28 | h1780-017 | 0.16 |
|  |  | h1779-014 | 0.20 |

Test Example 6: IL5 Antibodies Inhibit IL5-Induced Eosinophil Adhesion

IL5 can induce the differentiation, maturation, migration and activation of eosinophils, cause respiratory inflammation and lead to asthma. According to the principle that IL-5 cytokine can promote eosinophil adhesion and activate eosinophils, in this test example, the effects of IL-5 specific antibodies on blocking the IL-5-mediated pathway were determined by collecting and purifying eosinophils from human peripheral blood, and detecting in vitro the effects of IL-5 antibodies on blocking IL5-mediated eosinophil adhesion.

Specifically, human peripheral blood was 5-fold diluted with PBS containing 2 mM EDTA, monocytes and granulocytes were separated by Percoll™ (with density gradient of 1.088), the erythrocyte layer containing granulocytes was carefully aspirated, and the erythrocytes were removed with Red Blood Cell Lysis Buffer. The remaining cells were counted, Separating Magnetic Beads coated with human CD16 antibody (Miltenyi, Catalog No. 130-045-701) was added, incubated for 30 min and flowed through the magnetic bead column. Effluent of cell fraction was directly collected, which was mainly composed of eosinophils. The resulting eosinophils were counted and added into a 96-well cell culture plate pre-coated with IgG antibody, about $1\times10^4$ cells per well, added with human IL-5 (20 ng/ml) and different concentrations of IL-5 antibody molecules (starting at 10 μg/ml, 3-fold diluted, 10 levels of concentrations). The cell culture plate was incubated in an incubator at 37° C., 5% $CO_2$ for 1 h, and then added with 0.3% CTAB to lyse the cells. Finally, peroxidase reaction substrate TMB was added to develop color. The OD450 absorption values were read under microplate reader. The maximum adsorption value was read out in the well only added with IL-5, and the well containing neither IL-5 nor antibody drug was set as the background control. The inhibition value of each concentration of the antibody drugs relative to the maximum adsorption value was calculated as =(maximum adsorption value−[antibody drug])/(maximum adsorption value−background control value)×100%, and IC50 was calculated. The results are shown in Table 18:

TABLE 18

| IL-5 antibodies block IL-5-induced eosinophil adhesion | | | | |
| --- | --- | --- | --- | --- |
|  | Hu39D10 | h1705-008 | h1706-009 | h1780-017 |
| IC50 (ng/ml) | 11.79 | 4.85 | 4.3 | 21.19 |

The results indicate that the humanized antibodies of the present disclosure show strong ability to inhibit IL5-mediated eosinophil adhesion.

Test Example 7: Evaluation of Specificity of Humanized IL-5 Antibodies to Th2 Cytokines IL-5 is one of Th2 cytokines. To verify that IL-5 antibodies specifically target only IL-5 without cross-reactivity with other cytokines, 12 types of Th2 and related cytokines, including IL2(R&D, 202-IL-010/CF), IL4(R&D, 204-IL-050/CF), IL-5(R&D, 205-IL-025/CF), IFNgamma, IL6 (R&D, 7270-IL-025/CF), IL9(R&D, 209-IL-010/CF), IL10 (R&D, 217-IL-025/CF), IL13(R&D, 213-ILB-025/CF). IL25(R&D, 8134-IL-025/CF), IL31(R&D, 2824-IL-010/CF) and IL3 sharing a receptor with IL-5 (203-IL-050/CF) and GMCSF (R&D, 215-GM-010/CF), were used in Fortebio assay.

Figure 2:
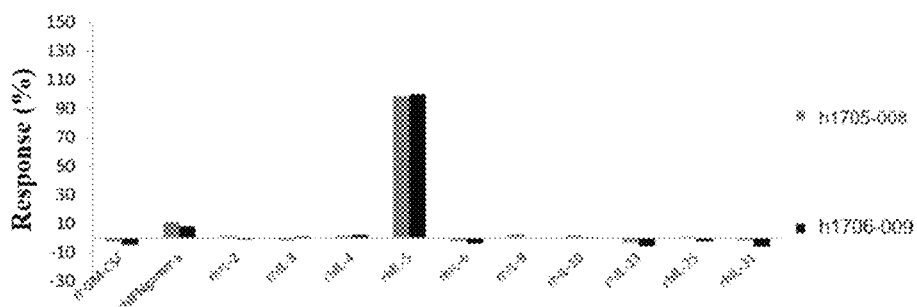
FIG. 2: Detection of binding specificity of IL-5 antibodies to Th2 cytokine.

Specifically, antibodies were captured by using Protein A Biosensor (PALL Fortebio, 18-5010), the capture signal was recorded, and then 40 nM of each cytokine was added and new binding signals were recorded. Finally, the binding signal for IL-5 was defined as 100%, and the binding signals between antibodies and other cytokines were observed. The results are shown in FIG. 2.

The results show that among the 12 types of the related cytokines, humanized IL-5 antibodies h1705-008 and h1706-009 merely specifically bind to IL-5, and do not show cross-reaction with other Th2 cytokines.

Pharmacokinetic Evaluation

Test Example 8: Pharmacokinetic Evaluation of Humanized IL-5 Antibodies in Rats

Experimental SD rats (provided by Sipple-BK Lab Animal Co., Ltd.), 18 males, were divided into 6 groups, with 3 rats in each group. Hu39D10, h1705-008 and h1706-009 were administered intravenously and subcutaneously. Another 9 SD rats were only administered intravenously with h1773-007, h1779-014 or h1780-017. For the intravenous administration group, 0.2 ml of whole blood was collected without introducing anticoagulation before administration and 5 min, 8 h, 1 d, 2 d, 4 d, 7 d, 10 d, 14 d, 21 d and 28 d after administration. The blood samples were placed at 4° C. for 30 min, centrifuged at 1000 g for 15 min. the supernatants (serum) were placed in EP tubes and stored at −80° C. For the subcutaneous administration group, whole blood was collected before administration and 1 h, 2 h, 4 h, 8 h, 1 d, 2 d, 4 d, 7 d, 10 d, 14 d, 21 d and 28 d after administration. The antibody concentration in the serum was determined by Elisa.

The results indicate that the humanized antibody molecules of the present disclosure have long half-life and high bioavailability in rats.

BSA and 0.6 mM EDTA was used for each time. The recovered volume of the lavage fluid was recorded.

BALF was centrifuged at 300 g at 4° C. for 5 minutes and the supernatant was retained for analysis of cytokines. After centrifugation, the cells were resuspended in 1.5 ml of PBS (containing 1% BSA and 0.6 mM EDTA) for cell counting. The total number of cells in BALF was counted with hemocytometer and Trypan blue stain assay. The cells were smeared, stained with Wright staining solution for one minute and then stained with Giemsa for 7 minutes to distinguish eosinophils, neutrophils, macrophages and lymphocytes. Cells were counted under optical microscope.

TABLE 19

Pharmacokinetic evaluation of Antibodies in rat

| | Hu39D10 | | h1705-008 | | h1706-009 | | h1773-007 | h1779-014 | h1780-017 |
|---|---|---|---|---|---|---|---|---|---|
| dosage | 5 mg/kg (IV) | 5 mg/kg (SC) | 5 mg/kg (IV) | 5 mg/kg (SC) | 5 mg/kg (IV) | 5 mg/kg (SC) | 5 mg/kg (IV) | 5 mg/kg (IV) | 5 mg/kg (IV) |
| bio-availability | | 68.4% | | 114.3% | | 59.6% | | | |
| T½ (day) | 15.1 ± 1.7 | 15.0 ± 4.2 | 15.7 ± 2.3 | 13.3 ± 3.7 | 20.1 ± 4.3 | 17.9 ± 0.5 | 18.2 ± 1.1 | 12.2 ± 0.3 | 14.6 ± 0.8 |

In Vivo Biological Evaluation

Test Example 9: Evaluation of Efficacies of IL-5 Antibodies in OVA-Induced Mouse Asthma Model This test example is to assess efficacies of IL-5 antibodies in ovalbumin (OVA) aerosol-induced BALB/c mouse asthma model based on airway inflammatory response and airway remodeling.

Mice were randomly divided into 7 groups according to body weight, 10 mice in each group: normal control group (G1); model group (G2); treatment groups for antibody h1705-008 (G3 and G4 for two dosages of 10 mpk and 2 mpk, respectively) and h1706-009 (G5 and G6 for two dosages of 10 mpk and 2 mpk, respectively); and a control group for positive antibody Hu39D10 (G7, 10 mpk). On day 1 and day 14, all mice were sensitized by intraperitoneal injection of sensitizing solution. On day 28, 29, and 30, six groups of mice excluding Group 1 were challenged with OVA aerosol challenging solution for 30 minutes. Two hours before the challenge, Group 2 (G2) were intraperitoneally injected with phosphate buffer, and Group 3-7 (G3-G7) mice were intraperitoneally injected with different doses of different antibodies, once a day, for three consecutive days. Fresh antibody solutions to be tested were prepared immediately before each injection and all injections were completed within half an hour. As normal control, 2 hours after intraperitoneal injection of phosphate buffer, the mice in Group 1 were challenged with aerosol PBS for 30 minutes, once a day, for three consecutive days.

On day 31, animals were tested for airway hyperresponsiveness by using WBP system. All animals inhaled spray of methacholine at doubly increasing concentration of 1.5625, 3.125, 6.25, 12.5, 25, 50 mg/mL to determine the enhanced exhalation intermittent value at the corresponding concentration.

On day 31, 1 hour after the test of airway response with WBP system, a trachea cannula with diameter of 1.2 mm was inserted into the trachea and fixed, lung lavage was performed twice, 0.8 ml of phosphate buffer containing 1%

After lavage, lung tissues were collected, immersed in 10% neutral formaldehyde solution and then fixed in 10% neutral formaldehyde solution. The fixed tissues were then subjected to paraffin embedding, trimming, H & E staining, and scoring. The test results are shown in FIG. 3 and FIGS. 4A and 4B.

Figure 3:
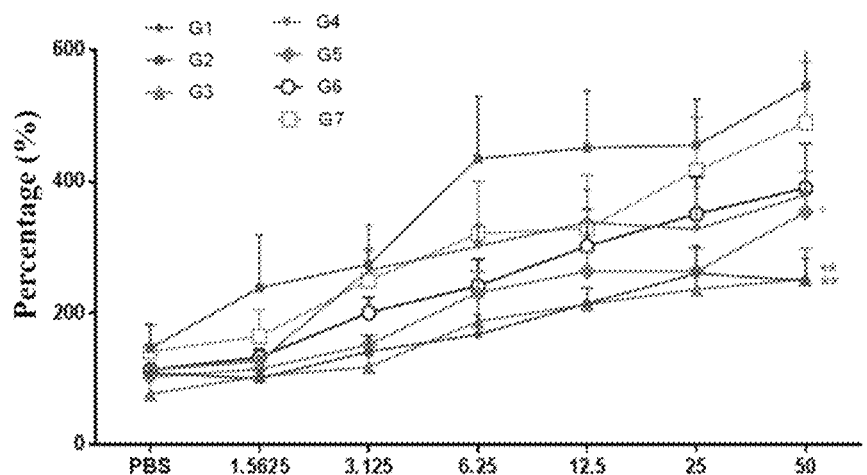
FIG. 3: IL-5 antibodies enhance respiratory intermittent value (Penh). G1: normal control group (PBS); G2: model group (IgG); G3: h1705-008 antibody 10mpk group; G4: h1705-008 antibody 2mpk group; G5: h1706-009 antibody 10 mpk group; G6: h1706-009 antibody 2mpk group; G7: Hu39D10 10mpk group; *$p<0.05$, **$<0.01$ (compared with G2 group by ANOVA/Bonferroni)
Figure 4A:
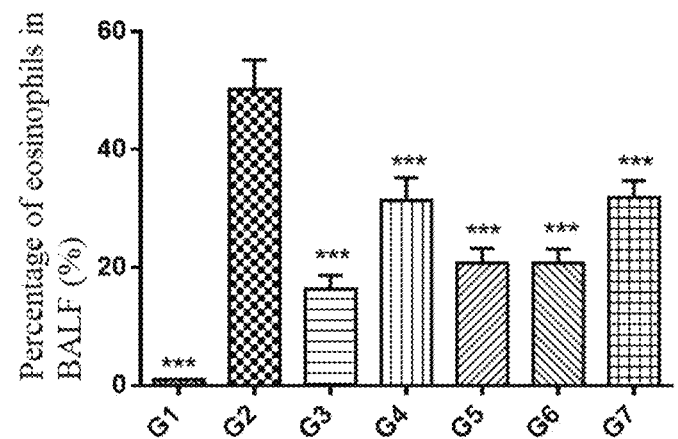
FIG. 4A: The level of BALF eosinophils in lung of asthma mice.
Figure 4B:
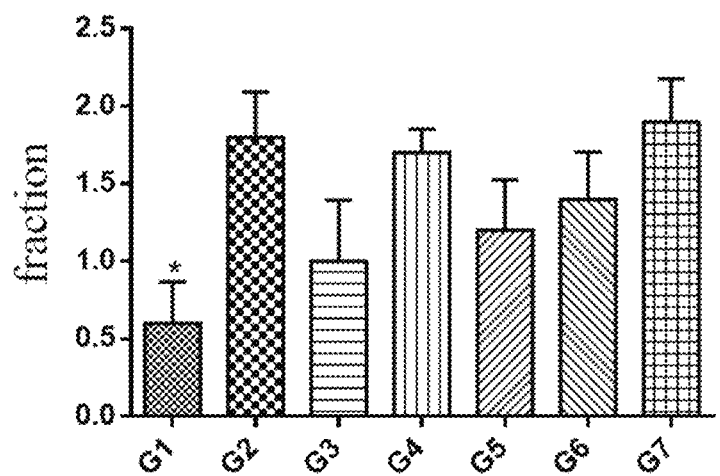
FIG. 4B: Scores of thickness of asthma mice tracheal mucosa. G1: normal control group; G2: model group; G3: h1705-008 antibody 10mpk group; G4: h1705-008 antibody 2mpk group; G5: h1706-009 antibody 10mpk group; G6: h1706-009 antibody 2mpk group; G7: Hu39D10 10mpk group.
Figure 4C:
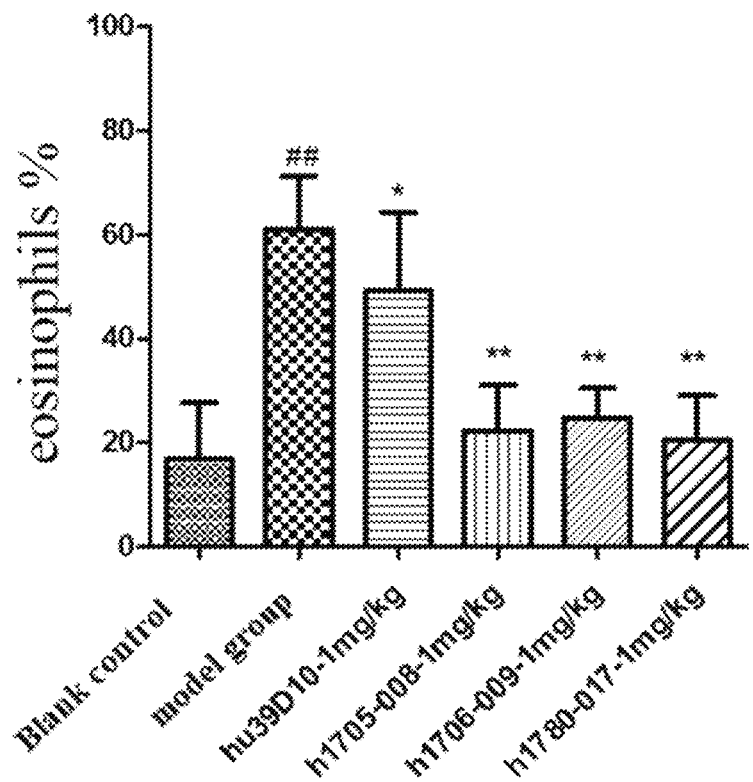
FIG. 4C: Percentage of BALF eosinophils in lung of asthma mice.

The results show that the antibody molecules h1705-008 and h1706-009 of the present disclosure can significantly improve lung function in a dose-dependent manner, while high dose (10 mpk) of positive compound cannot improve lung function (see FIG. 3). At the same time, the two antibodies significantly reduced the level of eosinophils and the thickness of mucosa, and exhibited stronger ability to reduce the amount of eosinophils compared to positive antibody at the same dosage (10 mpk) (see FIGS. 4A and 4B). By repeating the experiment in the same type of mouse asthma model, we also verified that 1 mg/ml of h1705-008, h1706-009 and h1780-017 all significantly reduced the level of eosinophils in BalF, when compared with the positive antibody (see FIG. 4C).

Figure 5A:
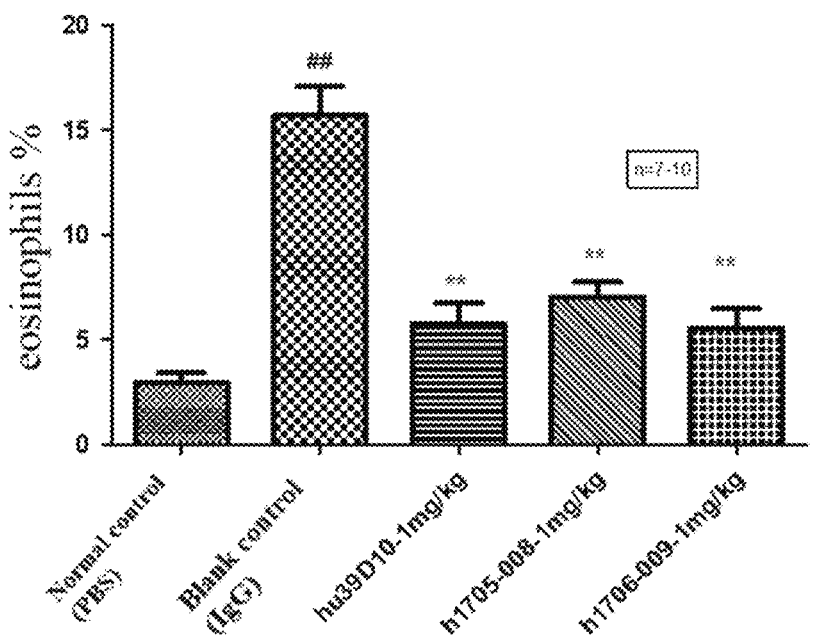
FIG. 5A and FIG. 5B show the ability of IL5 mAb to reduce the level of eosinophils in BALF.
Figure 5B:
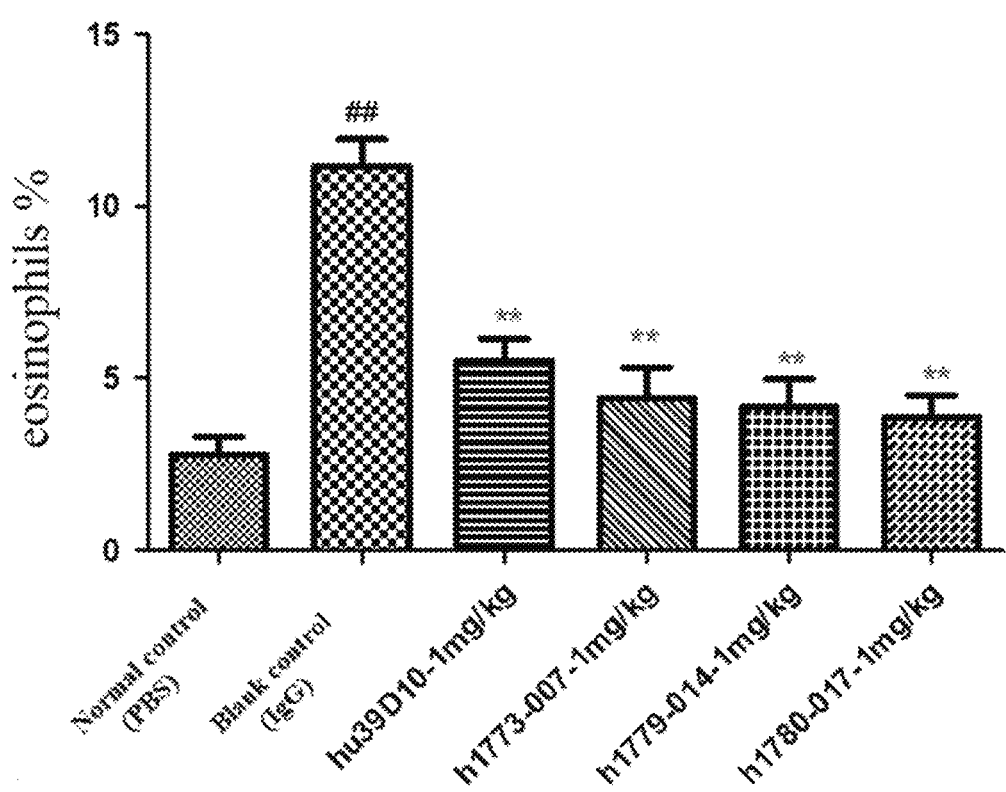

Test Example 10: Evaluation of In Vivo Efficacy of IL5 Antibodies in Exogenous Human IL5-Induced Acute Asthma in Guinea Pig Model In this test example, male guinea pigs were used to establish human IL5-induced acute asthma model, and hu39D10 was used as a positive antibody to evaluate whether the five humanized IL-5 monoclonal antibodies of the present disclosure have inhibition effects on human IL5-induced increase of eosinophils in Bronchoalveolar Lavage Fluid (BALF) in guinea pig. Guinea pigs were divided into 9 groups, 8-10 in each group: normal control group, model group, hu39D10 (1 mg/kg) group, h1705-008 (1 mg/kg) group, h1706-009 (1 mg/kg) group, h1780-017 (1 mg/kg) group, h1773-007 (1 mg/kg) group and h1779-014(1 mg/kg) group. On day 1, the guinea pigs in the model group and the drug-administration groups were intratracheally injected with 100 μl of human IL5 (containing 5 μg of IL5 antigen) for priming, and the normal control group were intratracheally injected with PBS. 2 hours after the priming, 1 mg/kg of the above IL5 monoclonal antibodies (at the administration volume of 5 ml/kg) were intraperitoneally administered to the drug-administration groups, the corresponding IgG antibody was administered to the model group, and PBS was intraperitoneally administered to the normal control group. 24 hours after intratracheal injection, the guinea pigs were anesthetized and bronchoalveolar lavage fluid was extracted. The cell concentration was adjusted to $5^10^6$/ml, and 15 μl of the same was dropped on the glass slide, dried and fixed for HE staining, and the total number of cells and the number of eosinophils were counted under 400× microscope. The percentage of eosinophils was calculated. The results are shown in FIGS. 5A and 5B, indicating that all of the five humanized antibodies of the present disclosure can significantly reduce the level of eosinophils in BALF.

Evaluation of Stability

Test Example 11: Stability of Humanized Anti-IL-5 Antibodies

1. Chemical Stability of Antibodies

Deamidation modification is a common chemical modification in antibodies which may affect the long-term stability. In particular, high degree of deamidation, oxidation or isomerization modification of partial amino acids in the CDR regions are generally to be avoided, or to be reduced by mutation. 100 μg samples taken at various time points were dissolved in 100 μl solution of 0.2 M His-HCl, 8 M Gua-HCl, pH 6.0, added with 3 μl of 0.1 g/mL DTT, incubated in water bath at 50° C. for 1 hour, and then ultrafiltered twice with 0.02 M His-HCl pH 6.0. 3 μl of 0.25 mg/mL trypsin was added, incubated in water bath at 37° C. overnight for enzymatic digestion. LC-MS analysis was performed with Agilent 6530 Q-TOF. The results show that the chemical stability of the humanized antibodies of the present disclosure was good, and the antibodies did not show abnormal modification after the acceleration reaction in 529 buffer system at 40° C. for one month.

2. Study on the Degree of Antibody Aggregation Under High Concentration Condition The stability of the test antibodies was evaluated at high concentrations and different buffer systems and different temperature conditions for one month. The stability was investigated at the concentration of 50 mg/ml, in three buffer systems of PB9, His and 529, at 40° C., 25° C., 4° C. and −80° C. with repeated freezing and thawing. The degree of aggregation was monitored by SEC-HPLC. Waters e2695 chromatograph was used, with the column of Waters Xbridge BEH 200A SEC, and the mobile phase was PBS (pH was adjusted to 6.8 with diluted hydrochloric acid). 50 μg of protein was loaded and isocratic elution was performed at a flow rate of 0.5 mL/min. It was observed that none of the humanized IL-5 antibodies significantly aggregated under high concentration conditions. After 4 weeks of acceleration reaction at 40° C., the purity of antibody monomer was greater than 95% in all three systems.

3. Study on the Purity of Antibodies Under High Concentration Conditions

The stability of the test antibodies was evaluated at high concentrations and different buffer systems and different temperature conditions for one month. The stability was investigated at the concentration of 50 mg/ml, in the His system and at 40° C. The purity was monitored by CE-SDS. 100 μg of protein was taken and sample buffer was added to reach 95 μl. For reducing mode analysis, 5 μl of dimercaptoethanol was added; for non-reducing mode analysis, 5 μl of IAA was added. Incubated in water bath at 70° C. for 10 min, centrifuged and the supernatant was loaded. Data was collected and analyzed with Beckman PA800plus electrophoresis apparatus. It was observed that the antibody proteins have good purity stability under high concentration conditions, and after 28 days of acceleration reaction at 40° C. CE-SDS analysis showed that the main peak of the antibodies was only decreased by 2%.

4. Detection of the Thermal Stability of Different Antibodies by UNIT

The samples were dissolved in corresponding buffer (PBS buffer), and the concentration of the samples was controlled at about 1 mg/ml. 9 μl was loaded. Parameter setting: starting temperature 20° C.; incubation 0 s; heating rate 0.3° C./min; Plate Hold 5 s; termination temperature 95° C. Tm values of the antibodies were detected. The antibodies have high Tm value and display good thermal stability.

The above described invention has been described in detail with the aid of the accompanying drawings and examples. However, the description and examples should not be construed as limiting the scope of the disclosure. The disclosures of all patents and scientific literatures cited herein are expressly incorporated by reference in their entirety.

The invention claimed is:

1. A monoclonal antibody or antigen-binding fragment thereof specifically binding to human IL-5, wherein the monoclonal antibody comprises a heavy chain variable region and a light chain variable region, wherein,
   (i) the heavy chain variable region comprises HCDR1, HCDR2 and HCDR3 region as set forth in amino acid sequences of SEQ ID NOs: 16-18; and the light chain variable region comprises LCDR1, LCDR2 and LCDR3 region as set forth in amino acid sequences of SEQ ID NOs: 19-21; or
   (ii) the heavy chain variable region comprises HCDR1, HCDR2 and HCDR3 region as set forth in amino acid sequences of SEQ ID NOs: 22-24; and the light chain variable region comprises LCDR1, LCDR2 and LCDR3 region as set forth in amino acid sequences of SEQ ID NOs: 25-27; or
   (iii) the heavy chain variable region comprises HCDR1, HCDR2 and HCDR3 region as set forth in amino acid sequences of SEQ ID NOs: 28-30; and the light chain variable region comprises LCDR1, LCDR2 and LCDR3 region as set forth in amino acid sequences of SEQ ID NOs: 31-33; or
   (iv) the heavy chain variable region comprises HCDR1, HCDR2 and HCDR3 region as set forth in amino acid sequences of SEQ ID NOs: 34-36; and the light chain variable region comprises LCDR1, LCDR2 and LCDR3 region as set forth in amino acid sequences of SEQ ID NOs: 37-39; or
   (v) the heavy chain variable region comprises HCDR1, HCDR2 and HCDR3 region as set forth in amino acid sequences of SEQ ID NOs: 40-42; and the light chain variable region comprises LCDR1, LCDR2 and LCDR3 region as set forth in amino acid sequences of SEQ ID NOs: 43-45; or
   (vi) the heavy chain variable region comprises HCDR1, HCDR2 and HCDR3 region as set forth in amino acid sequences of SEQ ID NOs: 34-36; and the light chain variable region comprises LCDR1, LCDR2 and LCDR3 region as set forth in amino acid sequences of SEQ ID NOs: 37-39.

2. The monoclonal antibody or antigen-binding fragment thereof according to claim 1, wherein the monoclonal antibody is a recombinant antibody selected from the group consisting of murine antibody, chimeric antibody, and humanized antibody.

3. The monoclonal antibody or antigen-binding fragment thereof according to claim 2, wherein the humanized antibody comprises a heavy chain variable region of SEQ ID NO: 49, 57, 63, 69 or 75.

4. The monoclonal antibody or antigen-binding fragment thereof according to claim 3, further comprising a back mutation, wherein the back mutation is selected from the group consisting of S49T, V93T and K98S, or a combination thereof on the heavy chain variable region of SEQ ID NO: 49, or the back mutation is selected from the group consisting of S49T, V93T and K98T, or a combination thereof on the heavy chain variable region of SEQ ID NO: 57, or the back mutation is selected from the group consisting of R38K, M48I, R67K, V68A, M70L, R72V, T74K and L83F, or a combination thereof on the heavy chain variable region of SEQ ID NO:63, or the back mutation is selected from the group consisting of F29I, R38K, V48I, R72A, T97F on the heavy chain variable region of SEQ ID NO:69, and N55V on CDR, or a combination thereof, or the back mutation is selected from the group consisting of R38K, M48I, R67K, V68A, R72A, T74K, M81L, L83F and D89E, or a combination thereof on the heavy chain variable region of SEQ ID NO:75.

5. The monoclonal antibody or antigen-binding fragment thereof according to claim 4, wherein the humanized antibody comprises a heavy chain variable region of SEQ ID NO:50 or 51, or comprises a heavy chain variable region of SEQ ID NO: 58 or 59, or comprises a heavy chain variable region selected from any one of SEQ ID NO: 64, 65 and 66, or comprises a heavy chain variable region of SEQ ID NO:70 or 71, or comprises a heavy chain variable region selected from any one of SEQ ID NOs: 76 to 79.

6. The monoclonal antibody or antigen-binding fragment thereof according to claim 2, wherein the humanized antibody comprises a light chain variable region of SEQ ID NO: 46, 54, 60, 67 or 72.

7. The monoclonal antibody or antigen-binding fragment thereof according to claim 6, further comprising a back mutation, wherein the back mutation is selected from the group consisting of A43 S, L47V, G66R, T69S, F71Y and Y87F or a combination thereof on the light chain variable region of SEQ ID NO:46; or the back mutation is selected from the group consisting of A43S, L47M, F71Y and Y87F or a combination thereof on the light chain variable region of SEQ ID NO: 54; or the back mutation is selected from the group consisting of E1D, I2T, I57V, V84T and Y86F or a combination thereof on the light chain variable region of SEQ ID NO: 60; or the back mutation is selected from the group consisting of M4L, A42S, L45P and L46W or a combination thereof on the light chain variable region of SEQ ID NO: 67; or the back mutation is selected from the group consisting of A43S, I48V and F71Y or a combination thereof on the light chain variable region of SEQ ID NO:72.

8. The monoclonal antibody or antigen-binding fragment thereof according to claim 7, wherein the humanized antibody comprises a light chain variable region of SEQ ID NO: 47 or 48; or comprises a light chain variable region of SEQ ID NO: 55 or 56; or comprises a light chain variable region of SEQ ID NO: 61 or 62; or comprises a light chain variable region of SEQ ID NO: 68; or comprises a light chain variable region of SEQ ID NO: 73 or 74.

9. The monoclonal antibody or antigen-binding fragment thereof according to claim 1, wherein the humanized antibody comprises:
   a heavy chain variable region selected from any one of SEQ ID NOs: 49-51 and a light chain variable region selected from any one of SEQ ID NOs: 46-48; or
   a heavy chain variable region selected from any one of SEQ ID NOs: 57-59 and a light chain variable region selected from any one of SEQ ID NOs: 54-56; or
   a heavy chain variable region selected from any one of SEQ ID NOs: 63-66 and a light chain variable region selected from any one of SEQ ID NOs: 60-62; or
   a heavy chain variable region selected from any one of SEQ ID NOs: 69-71 and a light chain variable region selected from any one of SEQ ID NOs: 67-68; or
   a heavy chain variable region selected from any one of SEQ ID NOs: 75-79 and a light chain variable region selected from any one of SEQ ID NOs: 72-74.

10. The monoclonal antibody or antigen-binding fragment thereof according to claim 1, wherein the antibody is a full length antibody, and further comprises a human antibody constant region, and wherein the full-length antibody comprises a human antibody heavy chain constant region as set forth in SEQ ID NO: 52 and a human light chain constant region as set forth in SEQ ID NO:53.

11. The monoclonal antibody or antigen-binding fragment thereof according to claim 1, wherein the antigen-binding fragment is selected from the group consisting of Fab, Fab', F(ab')2, single-chain antibody (scFv), dimerized V region (diabody), and disulfide-stabilized V region (dsFv).

12. A pharmaceutical composition comprising a therapeutically effective amount of the monoclonal antibody or antigen-binding fragment thereof according to claim 1, and one or more pharmaceutically acceptable carriers, diluents, buffers or excipients.

* * * * *